(12) United States Patent
Tsukii et al.

(10) Patent No.: US 8,345,237 B2
(45) Date of Patent: Jan. 1, 2013

(54) OPTICAL INFORMATION ANALYZING DEVICE AND OPTICAL INFORMATION ANALYZING METHOD

(75) Inventors: Ken Tsukii, Tokyo (JP); Kenichi Kimura, Tokyo (JP); Toru Takahashi, Tokyo (JP); Jie Xu, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 13/335,997

(22) Filed: Dec. 23, 2011

(65) Prior Publication Data

US 2012/0092667 A1  Apr. 19, 2012

Related U.S. Application Data

(63) Continuation of application No. PCT/JP2010/055810, filed on Mar. 31, 2010.

(51) Int. Cl.
*G01N 21/00* (2006.01)
(52) U.S. Cl. ........................................ 356/338
(58) Field of Classification Search .................. None
See application file for complete search history.

(56) References Cited

U.S. PATENT DOCUMENTS

| | | | |
|---|---|---|---|
| 5,194,921 A * | 3/1993 | Tambo et al. | 356/432 |
| 6,184,983 B1 * | 2/2001 | Yamaguchi et al. | 356/335 |
| 7,957,002 B2 | 6/2011 | Tsukii et al. | |
| 2006/0152707 A1 | 7/2006 | Kanda | |
| 2010/0233753 A1 | 9/2010 | Tsukii et al. | |
| 2011/0199612 A1 | 8/2011 | Tsukii et al. | |

FOREIGN PATENT DOCUMENTS

| | | |
|---|---|---|
| JP | 62-87831 | 4/1987 |
| JP | 7-318478 | 12/1995 |
| JP | 2006-170687 | 6/2006 |
| JP | 3891925 B2 | 12/2006 |
| JP | 2008-292448 | 12/2008 |

OTHER PUBLICATIONS

International Search Report issued Jul. 6, 2010, in PCT/JP2010/055810.
Office Action issued Apr. 8, 2011, in Japanese Patent Application No. 2010-550935 (with English-language translation).
U.S. Appl. No. 12/403,701, filed Mar. 13, 2009, Tsukii, et al.
U.S. Appl. No. 13/337,848, filed Dec. 27, 2011, Tsukii, et al.

* cited by examiner

*Primary Examiner* — Tu Nguyen
(74) *Attorney, Agent, or Firm* — Oblon, Spivak, McClelland, Maier & Neustadt, L.L.P.

(57) ABSTRACT

An optical information analyzing device includes an irradiating unit that irradiates irradiation light to specimens, a transmitted light receiving unit that receives transmitted light and detects the transmitted light as a transmitted light signal, a scattering/fluorescent light receiving unit that receives lateral scattering light and fluorescent light and detects the lateral scattering light and the fluorescent light as a scattering/fluorescent light signal, a nozzle position adjusting mechanism, and an analyzing unit that measures the optical information on the specimen on the basis of the detected transmitted light signal and the detected scattering/fluorescent light signal and analyzes the specimen.

19 Claims, 12 Drawing Sheets

OPTICAL INFORMATION ANALYZING DEVICE AND OPTICAL INFORMATION ANALYZING METHOD

TECHNICAL FIELD

The present invention relates to an optical information analyzing device and an optical information analyzing method. In particular, the present invention relates to an optical information analyzing device and an optical information analyzing method that measure optical information on specimens by irradiating irradiation light onto the specimens, which are objects to be measured and are dispersed in a liquid flowing through a flow passage.

BACKGROUND ART

There is proposed a device (flow cytometer or cell sorter) for obtaining biological information on biological particles by allowing a liquid, which contains dyed biological particles (minute objects to be detected: specimens), to flow into a flow passage of a flow passage-forming member (flow cell), irradiating the biological particles with light illuminated from an illuminating unit (irradiating unit), and detecting scattering light or fluorescent light emitted from the biological particle with a detecting unit (light receiving unit) (for example, see Patent Document 1).

In the past, in connection with the above-mentioned device, a sample flow is adjusted in a manner such that the flow of the liquid flowing through the flow passage of the flow cell is surrounded by a sheath flow and is present near the center of the flow passage, and a light receiving unit is configured such that an optical axis and a focal point of an optical system of the light receiving unit are aligned with and fixed at the center of the flow passage of the flow cell on a plane substantially perpendicular to the sample flow. Further, the irradiating unit is configured such that, when condensed irradation light is irradiated onto the sample flow and scattering light or fluorescent light from the specimens is received, the irradiating unit can optimally adjust the position of the optical axis thereof relative to the sample flow while actually irradiating the sample flow with irradiation light and checking the optical information, in order to obtain scattering light or fluorescent light with high sensitivity or obtain the optical information on specimens with a small variation.

PRIOR ART DOCUMENT

Patent Document

Patent Document 1: Japanese Patent No. 3,891,925

DISCLOSURE OF THE INVENTION

Problems to be Solved by the Invention

However, the above-mentioned device in the related art has a problem in that, when a sample flow passes through a position deviated from the center of the flow passage of the flow cell, the optical axis of the optical system of the light receiving unit does not intersect the sample flow and the optical axis of the irradiating unit since the optical axis of the irradiating unit is aligned with the sample flow. For this reason, the light receiving unit is configured to be capable of receiving light in the wide range. As a result, the sensitivity of the detected scattering light or fluorescent light is lowered or the obtained optical information on the specimens has variations.

Further, adjustment of the optical axis of the irradiating unit can be carried out only while actually forming a sample flow by making the liquid flow into the flow passage of the flow cell. For this reason, there is a problem in that it may not be possible to easily adjust the optical axis of the irradiating unit.

The invention has been made to solve the above-mentioned problems, and an object of the invention is to provide an optical information analyzing device and an optical information analyzing method in which a light receiving unit for receiving transmitted light is provided at a position directly facing an irradiating unit and which may increase the sensitivity of the received transmitted light by adjusting the position of a sample flow relative to a measurement region in a flow passage and measure the optical information on specimens with a small variation.

Means for Solving the Problems

The following invention is provided to solve the above-mentioned problems in the related art.

An optical information analyzing device according to a first aspect of the invention is an optical information analyzing device for measuring optical information on specimens by irradiating single-mode irradiation light onto the specimens, which are objects to be measured and are dispersed in a liquid flowing through a flow passage. The optical information analyzing device includes a flow cell that has the flow passage, an introduction nozzle that introduces the liquid into the flow passage of the flow cell, an irradiating unit that irradiates irradiation light onto the liquid flowing through the flow passage of the flow cell, a transmitted light receiving unit that is provided at a position directly facing the irradiating unit with the flow cell interposed therebetween, receives transmitted light, which is the irradiation light irradiated from the irradiating unit and transmitted through the liquid, and detects the transmitted light as a transmitted light signal, and an analyzing unit that measures the optical information on the specimens on the basis of the transmitted light signal detected by the transmitted light receiving unit and analyzes the specimens. The transmitted light receiving unit is disposed in a manner such that a light receiving surface substantially perpendicular to an optical axis faces the irradiating unit and the center of the light receiving surface is substantially aligned with an optical axis of the irradiating unit. A diameter d" of the light receiving surface of the transmitted light receiving unit and an irradiation diameter D of the irradiation light that is irradiated from the irradiating unit onto the light receiving surface of the transmitted light receiving unit satisfy a relational expression of "d"$\leq$D."

Here, the single mode means a single transverse mode, and is preferably Gaussian distribution. However, intensity distribution is partially substantially uniform or a beam may be formed in an elliptical shape in the case of a certain object to be measured. Meanwhile, it is preferable that the intensity of irradiation light be uniform. Further, the irradiation diameter D is the diameter of a beam and means the diameter corresponding to $1/e^2$ (=13.5%) of the intensity of a beam at the center of a beam.

In connection with the introduction nozzle, an end portion thereof may not be formed in a protruding shape, and it is satisfactory if the introduction nozzle has a hole through which a liquid flows.

Moreover, light that is received by the transmitted light receiving unit, such as light that has passed through the liquid in which specimens are dispersed, light that has passed through the specimens, or light that is reflected, scattered, or diffracted by the specimens is called the transmitted light. The transmitted light signal is a signal that is obtained by converting the transmitted light into an electric signal. Light is received in an arbitrary region that receives the transmitted light, and the amount of light received (transmitted light signal) changes while a specimen is subjected to measurement. An area, a width, a peak, and the like of the change of the amount of received light are called optical information.

According to the optical information analyzing device according to a second aspect of the invention, in the optical information analyzing device according to the first aspect of the invention, the transmitted light receiving unit may include an optical fiber disposed such that a light receiving surface substantially perpendicular to the optical axis faces the irradiating unit. A core diameter d of the optical fiber and an irradiation diameter D of the irradiation light that is irradiated from the irradiating unit onto the light receiving surface of the optical fiber may satisfy a relational expression of "$d \leq D$."

Here, the core diameter d complies with JIS C 6820 (the general principle of an optical fiber).

According to the optical information analyzing device according to a third aspect of the invention, in the optical information analyzing device according to the second aspect of the invention, a clad diameter d' of the optical fiber and an outer irradiation diameter D' of the irradiation light that is irradiated from the irradiating unit onto the light receiving surface of the optical fiber may further satisfy a relational expression of "$D' \leq d'$."

Here, the clad diameter d' complies with JIS C 6820 (the general principle of an optical fiber). Further, the outer irradiation diameter D' means the diameter corresponding to 5% of the intensity of a beam at the center of a beam.

According to the optical information analyzing device according to a fourth aspect of the invention, the optical information analyzing device according to any one of the first to third aspects of the invention may further include an adjustment unit that adjusts the position of a sample flow, which is generated by the liquid in the flow passage, relative to a measurement region in the flow passage that is determined on the basis of the structure of the irradiating unit and the transmitted light receiving unit.

Here, the sample flow means the flow of the liquid that contains specimens when the liquid flows through the flow passage of the flow cell. Further, the center of the sample flow means the central position of a range, through which the sample flow passes, on the plane perpendicular to the flow direction of the sample flow. Furthermore, the position of the sample flow in the flow passage means a position, through which the center of the sample flow passes, on the plane in the flow passage perpendicular to the flow direction of the sample flow.

According to the optical information analyzing device according to a fifth aspect of the invention, the optical information analyzing device according to any one of the first to fourth aspects of the invention may further include one or more scattering/fluorescent light receiving units. The scattering/fluorescent light receiving units are provided at positions not directly facing the irradiating unit of which the optical axis intersects the optical axis of the irradiating unit, receive lateral scattering light and/or fluorescent light, which are the irradiation light irradiated from the irradiating unit and emitted from the specimens, and detect the receive lateral scattering light and/or fluorescent light as a scattering/fluorescent light signal.

According to the optical information analyzing device according to a sixth aspect of the invention, in the optical information analyzing device according to the fifth aspect of the invention, each of the scattering/fluorescent light receiving units may include an optical fiber disposed such that a light receiving surface substantially perpendicular to the optical axis does not face the irradiating unit.

According to the optical information analyzing device according to a seventh aspect of the invention, in the optical information analyzing device according to the fifth or sixth aspect of the invention, the optical axis of the irradiating unit and the optical axis of each of the scattering/fluorescent light receiving units may be substantially perpendicular to each other.

According to the optical information analyzing device according to an eighth aspect of the invention, in the optical information analyzing device according to any one of the fourth to seventh aspects of the invention, the position of the sample flow in the flow passage may be adjusted relatively so that a substantial center of the sample flow passes through a substantial center of the measurement region.

Here, the measurement region is determined on the basis of the diameter of the irradiation light irradiated from the irradiating unit in the flow passage or the light receiving region of the transmitted light receiving unit or the scattering/fluorescent light receiving unit. Further, the substantial center of the measurement region means a substantially central position of the length of the optical axis in the measurement region on the optical axis of the transmitted light receiving unit and the irradiating unit that are substantially aligned with each other.

According to the optical information analyzing device according to a ninth aspect of the invention, in the optical information analyzing device according to the fourth to seventh aspects of the invention, the adjustment unit may relatively adjust the position of the sample flow in the flow passage so that the substantial center of the sample flow intersects the optical axis of at least desired one of the scattering/fluorescent light receiving units and passes through a position distant from the scattering/fluorescent light receiving unit of which the optical axis intersects the substantial center of the sample flow as compared to the substantial center of the measurement region.

According to the optical information analyzing device according to a tenth aspect of the invention, in the optical information analyzing device according to the fourth to ninth aspects of the invention, the adjustment unit may include a nozzle position adjusting mechanism that adjusts the position of an end portion of the introduction nozzle in the flow passage of the flow cell. The position of the end portion of the introduction nozzle in the flow passage of the flow cell may be adjusted by the nozzle position adjusting mechanism, so that the position of the sample flow is adjusted relative to the measurement region.

According to the optical information analyzing device according to an eleventh aspect of the invention, in the optical information analyzing device according to the fourth and ninth aspects of the invention, the adjustment unit may include a plurality of offset jigs where the introduction nozzle is mounted and the position of the end portion of the introduction nozzle varies and which adjusts the position of the end portion of the introduction nozzle in the flow passage of the flow cell by being fixed the flow cell. The position of the end portion of the introduction nozzle in the flow passage may be adjusted so that the sample flow is positioned at a desired position relative to the measurement region, by an optimum offset jig selected among the plurality of offset jigs.

According to the optical information analyzing device according to a twelfth aspect of the invention, in the optical information analyzing device according to the first to eleventh aspects of the invention, the irradiating unit may include an optical fiber that propagates the irradiation light.

According to the optical information analyzing device according to a thirteenth aspect of the invention, the optical information analyzing device according to the first to twelfth aspects of the invention may further include an irradiation position adjusting mechanism. The irradiation position adjusting mechanism adjusts the direction and position of the optical axis of the irradiating unit and adjusts a distance between the irradiating unit and the light receiving surface of the transmitted light receiving unit so that the relational expression is satisfied.

An optical information analyzing method according to a first aspect of the invention is an optical information analyzing method of measuring optical information on specimens by introducing a liquid in which specimens, objects to be measured, are dispersed into a flow passage of a flow cell through an introduction nozzle and irradiating single mode irradiation light to the specimens, which are dispersed in the liquid flowing through the flow passage. The optical information analyzing method includes (a) a step of substantially aligning an optical axis of a transmitted light receiving unit with an optical axis of an irradiating unit, in which the transmitted light receiving unit is provided at a position directly facing the irradiating unit with the flow cell interposed therebetween, receives transmitted light, which is the irradiation light irradiated from the irradiating unit and transmitted through the liquid, and detects the transmitted light as a transmitted light signal, and (b) a step of performing adjustment so that a diameter d" of the light receiving surface of the transmitted light receiving unit and an irradiation diameter D of the irradiation light that is irradiated from the irradiating unit on the light receiving surface of the transmitted light receiving unit satisfy a relational expression of "$d'' \leq D$."

According to the optical information analyzing method according to a second aspect of the invention, when the transmitted light receiving unit includes an optical fiber and is disposed so that a light receiving surface substantially perpendicular to an optical axis of the fiber faces the irradiating unit, adjustment may be performed in the step (b) of the optical information analyzing method according to the first aspect of the invention so that a core diameter d of the optical fiber and an irradiation diameter D of the irradiation light irradiated from the irradiating unit on the light receiving surface of the optical fiber satisfy a relational expression of "$d \leq D$."

According to the optical information analyzing method according to a third aspect of the invention, adjustment may be performed in the step (b) of the optical information analyzing method according to the second aspect of the invention so that a clad diameter d' of the optical fiber and an outer irradiation diameter D' of the irradiation light irradiated from the irradiating unit on the light receiving surface of the optical fiber satisfy a relational expression of "$D' \leq d'$."

According to the optical information analyzing method according to a fourth aspect of the invention, the optical information analyzing method according to the first to third aspects of the invention may further include (c) a step of adjusting the position of a sample flow, which is generated by the liquid in the flow passage, relative to a measurement region in the flow passage that is determined on the basis of the structure of the irradiating unit and the transmitted light receiving unit, after the step (b).

According to the optical information analyzing method according to a fifth aspect of the invention, in the optical information analyzing method according to the fourth aspect of the invention, the step (c) may relatively adjust the position of the sample flow in the flow passage so that a substantial center of the sample flow passes through a substantial center of the measurement region.

According to the optical information analyzing method according to a sixth aspect of the invention, the optical information analyzing method according to the fourth aspect of the invention may further include (d) a step of receiving lateral scattering light and/or fluorescent light, which are the irradiation light irradiated from the irradiating unit and emitted from the specimens, and detecting the receive lateral scattering light and/or fluorescent light as a scattering/fluorescent light signal, and aligning the substantial center of the measurement region with a substantial center of a second measurement region determined on the basis of the structure of one or more scattering/fluorescent light receiving units that are provided at positions not directly facing the irradiating unit, before the step (c). The step (c) may relatively adjust the position of the sample flow in the flow passage so that a substantial center of the sample flow passes through a substantial center of the measurement region.

According to the optical information analyzing method according to a seventh aspect of the invention, the optical information analyzing method according to the fourth aspect of the invention may further include (d) a step of receiving lateral scattering light and/or fluorescent light, which are the irradiation light irradiated from the irradiating unit and emitted from the specimens, and detecting the receive lateral scattering light and/or fluorescent light as a scattering/fluorescent light signal, and aligning the substantial center of the measurement region with a substantial center of a second measurement region determined on the basis of the structure of one or more scattering/fluorescent light receiving units that are provided at positions not directly facing the irradiating unit, before the step (c). The step (c) may relatively adjust the position of the sample flow in the flow passage so that a substantial center of the sample flow intersects the optical axis of at least desired one of the scattering/fluorescent light receiving units as compared to the substantial center of the measurement region and passes through a position distant from the scattering/fluorescent light receiving unit of which the optical axis intersects the substantial center of the sample flow.

According to the optical information analyzing method according to an eighth aspect of the invention, in the optical information analyzing method according to the sixth or seventh aspect of the invention, the step (d) may make the optical axis of the scattering/fluorescent light receiving unit and the optical axis of the irradiating unit be substantially perpendicular to each other in the measurement region.

According to the optical information analyzing method according to a ninth aspect of the invention, in the optical information analyzing method according to any one of the fourth to eighth aspects of the invention, the step (c) may adjust the position of the sample flow relative to the measurement region by a nozzle position adjusting mechanism that adjusts the position of an end portion of the introduction nozzle in the flow passage of the flow cell.

According to the optical information analyzing method according to a tenth aspect of the invention, in the optical information analyzing device according to any one of the fourth to eighth aspects of the invention, the step (c) may adjust the position of the end portion of the introduction nozzle in the flow passage so that the sample flow is positioned at a desired position relative to the measurement region, by an optimum offset jig selected among a plurality of offset jigs where the introduction nozzle is mounted and the position of the end portion of the mounted introduction nozzle varies and which adjusts the position of the end portion of the introduction nozzle in the flow passage of the flow cell by being fixed to the flow cell.

Effects of the Invention

According to the optical information analyzing device and the optical information analyzing method of the invention, the transmitted light receiving unit for receiving the transmitted light is provided at the position directly facing the irradiating unit. Accordingly, it may be possible to increase the sensitivity of the transmitted light that is received by the transmitted light receiving unit.

Further, it may be possible to increase the sensitivity of the transmitted light received by the transmitted light receiving unit and to obtain the optical information on specimens with a small variation by aligning the optical axis of the transmitted light receiving unit with the optical axis of the irradiating unit and relatively adjusting the position of the sample flow so that the sample flow is perpendicular to the optical axis of the transmitted light receiving unit and the optical axis of the irradiating unit.

Furthermore, it may be possible to increase the sensitivity of the lateral scattering light or fluorescent light received by the scattering/fluorescent light receiving unit and to obtain the optical information on specimens with a small variation by relatively adjusting the position of the sample flow so that the sample flow is perpendicular to the intersection between the optical axis of the irradiating unit and the optical axis of the scattering/fluorescent light receiving unit that receives lateral scattering light or fluorescent light.

Moreover, in the case of a certain specimen, it may also be possible to improve the light receiving efficiency of a fluorescent ingredient of a surface antibody.

BEST MODE(S) FOR CARRYING OUT THE INVENTION

Hereinafter, an embodiment of the invention will be described in detail with reference to the drawings.

Figure 1:
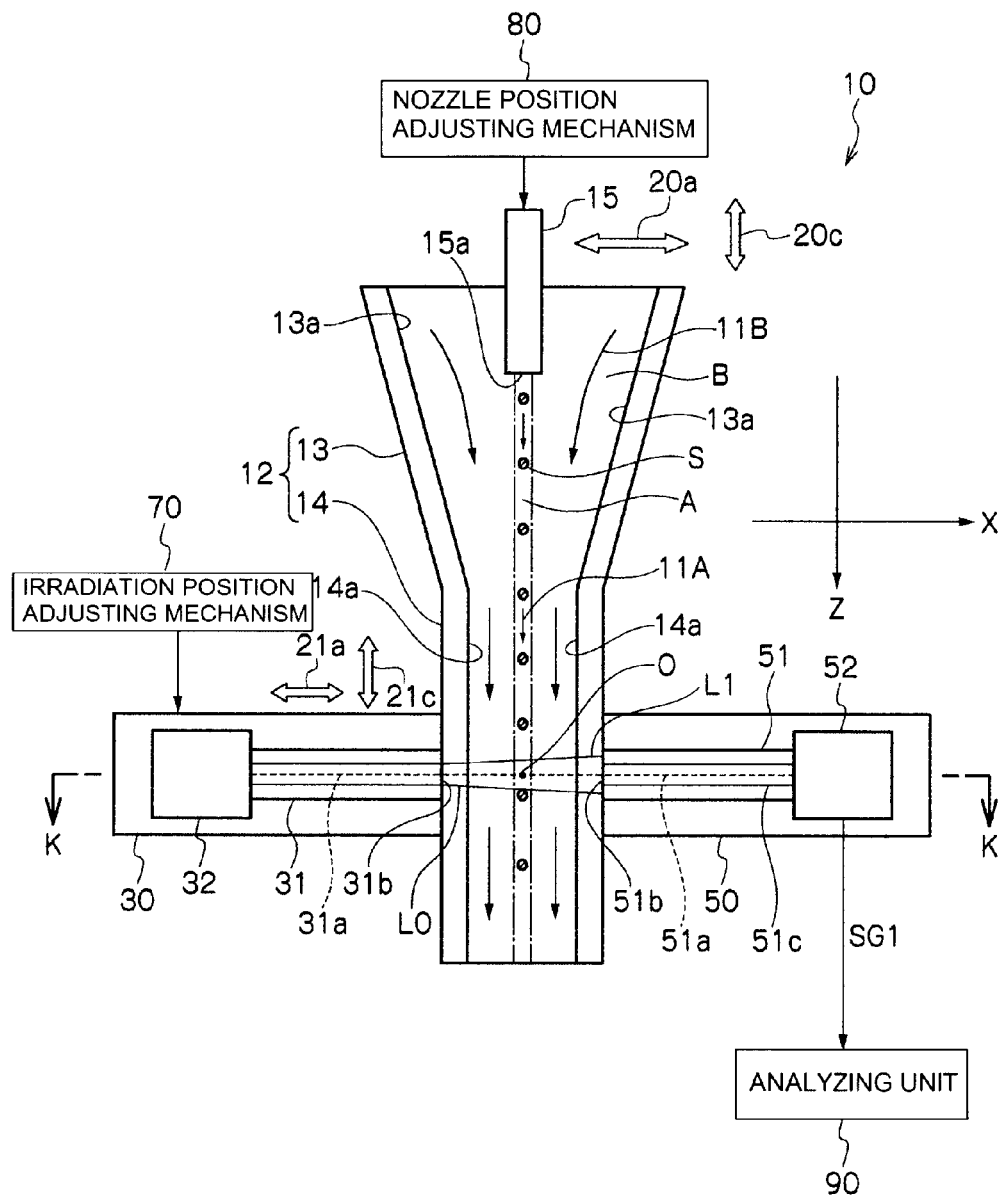
FIG. 1 is a schematic longitudinal sectional view of an optical information analyzing device according to an embodiment of the invention.

FIG. 1 is a schematic longitudinal sectional view of an optical information analyzing device according to an embodiment of the invention. Further, FIG. 2 is a schematic longitudinal sectional view of the optical information analyzing device of FIG. 1 that is rotated about a Z axis by an angle of 90°, and FIG. 3 is a schematic cross-sectional view of the optical information analyzing device of FIGS. 1 and 2 taken along the line K-K.

Figure 2:
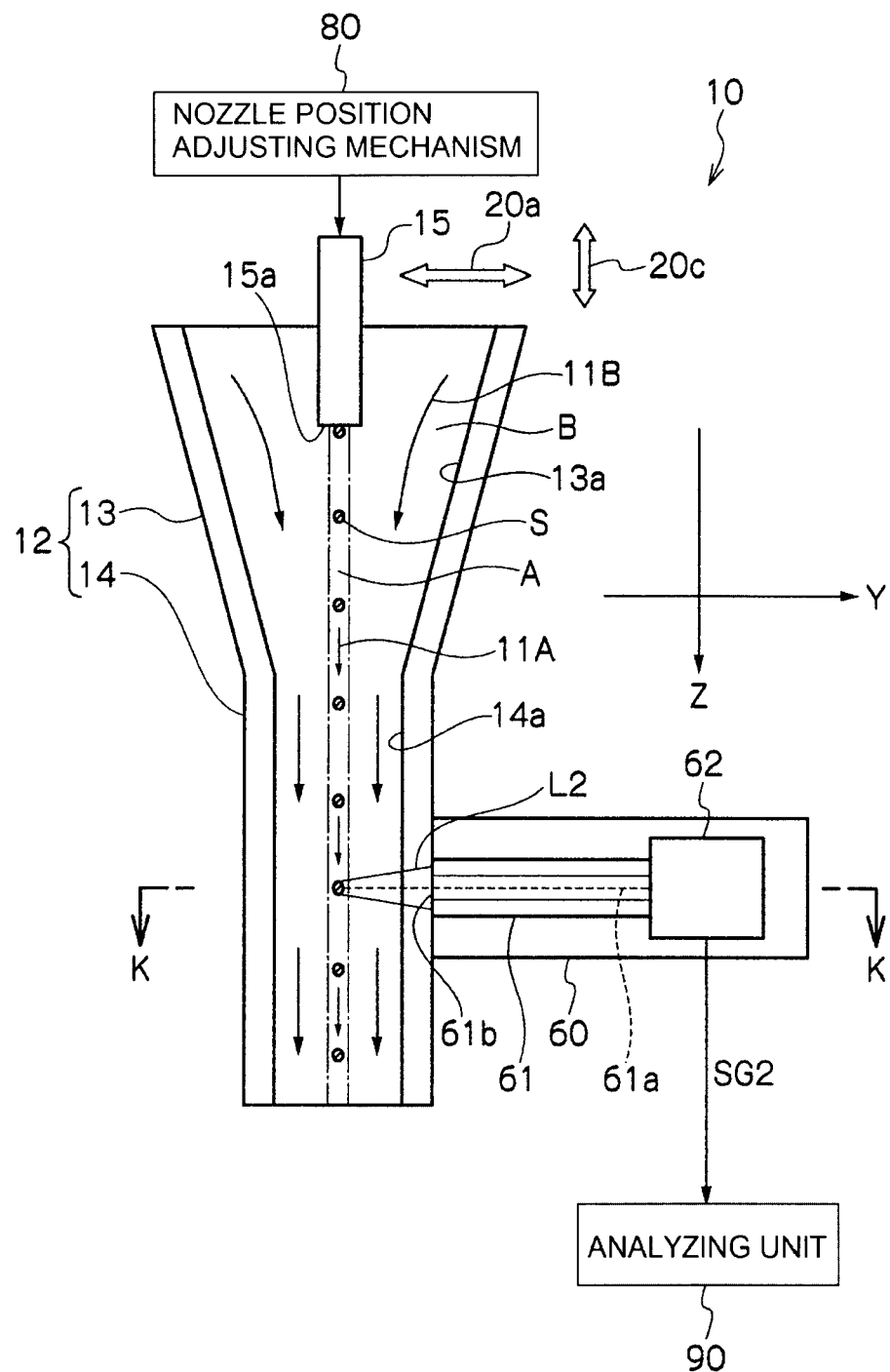
FIG. 2 is a schematic longitudinal sectional view of the optical information analyzing device of FIG. 1 that is rotated about a Z axis by an angle of 90°.
Figure 3:
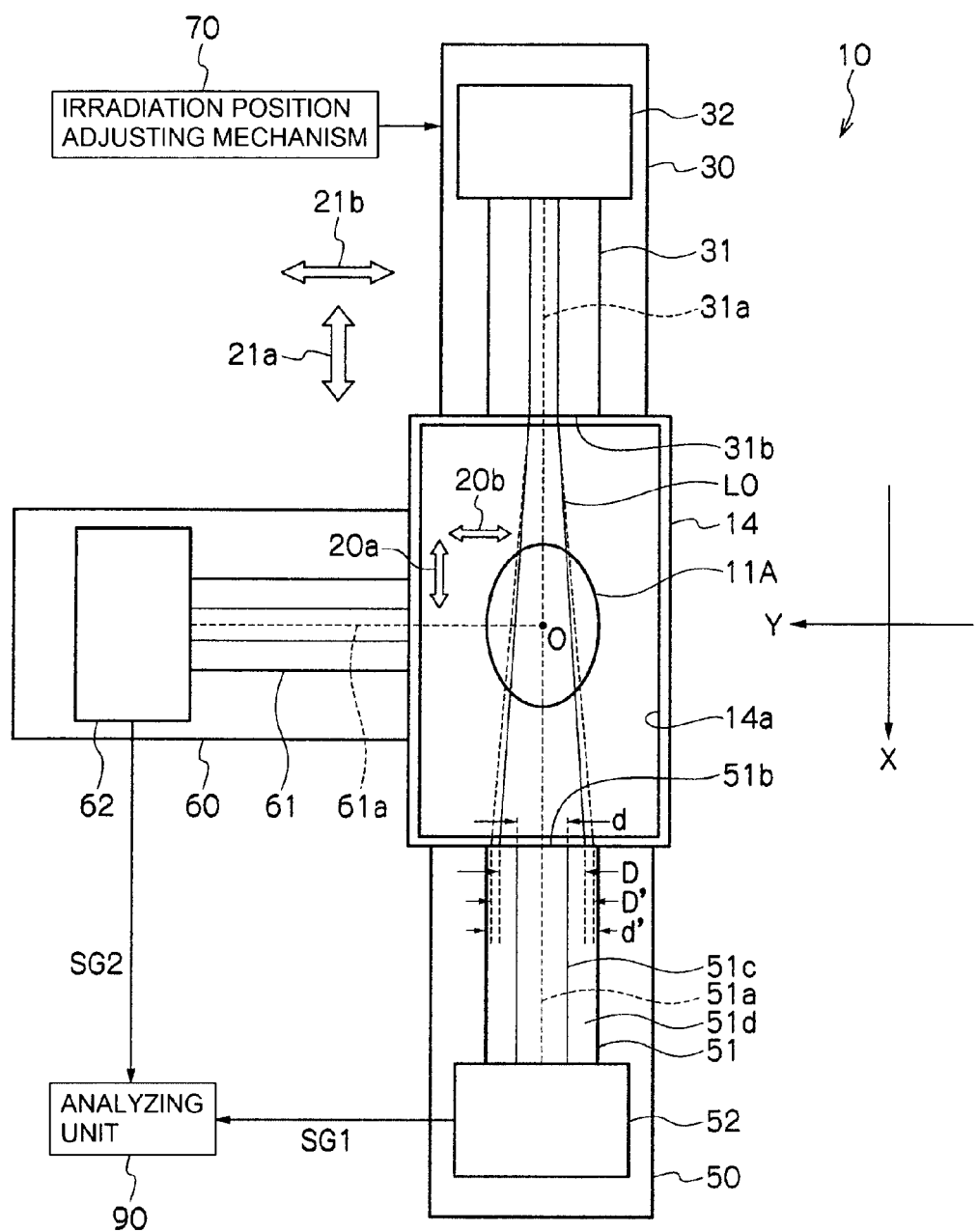
FIG. 3 is a schematic cross-sectional view of the optical information analyzing device of FIGS. 1 and 2 taken along the line K-K.

As illustrated in FIGS. 1 to 3, an optical information analyzing device 10 according to an embodiment of the invention includes a flow cell 12 that includes flow passages 13a and 14a through a liquid A flows; an introduction nozzle 15 that introduces the liquid A into the flow passage 13a of the flow cell 12 from a specimen storage portion (not illustrated); an irradiating unit 30 that irradiates single-mode irradiation light (excitation light) L0 to specimens S, which are objects for measurement and are dispersed in the liquid A flowing through the flow passage 14a of the flow cell 12; a transmitted light receiving unit 50 that receives transmitted light L1, which is the excitation light having been transmitted through the specimen S, and detects the transmitted light as a transmitted light signal SG1; a scattering/fluorescent light receiving unit 60 that receives lateral scattering light and fluorescent light L2 from the specimen S and detects the lateral scattering light and the fluorescent light as a scattering/fluorescent light signal SG2; an irradiation position adjusting mechanism 70 that adjusts the position of the irradiating unit 30; a nozzle position adjusting mechanism 80 that adjusts the position of an end portion 15a of the introduction nozzle 15 so as to align the position of the end portion of the introduction nozzle with the transmitted light receiving unit 50 and the irradiating unit 30; and an analyzing unit 90 that measures the optical information on the specimen S on the basis of the transmitted light signal SG1 detected by the transmitted light receiving unit 50 and the scattering/fluorescent light signal SG2 detected by the scattering/fluorescent light receiving unit 60, and analyzes the specimen S. The optical information analyzing device irradiates non-condensed irradiation light L0 to the specimens S, which are dispersed in the liquid A flowing through the flow passage, from the irradiating unit 30 and measures the optical information on the specimen S on the basis of the transmitted light signal SG1 and the scattering/fluorescent light signal SG2 of the specimen S that are detected by the transmitted light receiving unit 50 and the scattering/fluorescent light receiving unit 60.

In this specification, light, such as light transmitted through the liquid where the specimens are dispersed, light transmitted through the specimens, and light reflected, scattered, and diffracted by the specimens, which is received by a transmitted light receiving unit, is called the transmitted light. Further, the transmitted light signal is a signal that is obtained by converting the transmitted light into an electric signal, and the scattering/fluorescent light signal is a signal that is obtained by converting the lateral scattering light and/or the fluorescent light into an electric signal. Furthermore, since light is received in an arbitrary region that receives the transmitted light, the amount of received light (the transmitted light signal) changes during the measurement of the specimens. An area, a width, a peak, and the like of this change are called transmitted light information. Moreover, an area, a width, a peak, and the like of the change of the amount of received lateral scattering light and/or fluorescent light during the measurement of the specimens are also called transmitted light information.

The flow cell 12 includes a tapered portion 13 including a tapered flow passage 13a and a capillary portion 14 including a flow passage 14a. The tapered flow passage 13a forms a flow 11B of a sheath liquid B so that the flow 11B of the sheath liquid B surrounds the flow of the liquid A in which the specimens S are dispersed. Further, the tapered flow passage forms a linear flow 11A of the liquid A in a Z direction. The capillary portion 14 maintains the linear flow 11A of the liquid A in the Z direction and is linear in the Z direction. The flow passage 14a has a rectangular cross-section taken along a direction perpendicular to the Z direction. The tapered portion 13 and the capillary portion 14 are integrally formed so that the flow passage 13a and the flow passage 14a communicate with each other. Further, the flow cell 12 is made of glass or a transparent resin.

In this specification, the term "sample flow" means the flow 11A of the sample liquid A when the liquid (sample liquid) A containing the specimens S flows through the flow passages 13a and 14a of the flow cell 12, and the term "sheath flow" means the flow 11B of the sheath liquid B that surrounds the sample flow. Further, the direction of the sample flow 11A is referred to as the Z direction. Furthermore, a direction, which is perpendicular to the Z direction and is substantially parallel to the direction of an optical axis of the transmitted light receiving unit 50 to be described below (the direction of an optical axis 51a of an optical fiber 51) and the direction of an optical axis of the irradiating unit 30 (the direction of an optical axis 31a of an optical fiber 31), is referred to as an X direction. Moreover, a direction, which perpendicular to the Z direction and the X direction, is referred to as a Y direction.

The introduction nozzle 15 introduces the sample liquid A into the flow passage 13a of the flow cell 12 from a specimen storage portion (not illustrated). Further, the introduction nozzle 15 is configured such that the end portion 15a thereof can be freely moved in the flow passage 13a of the flow cell 12 in the X direction (the direction of an arrow 20a), the Y direction (the direction of an arrow 20b), and the Z direction (the direction of an arrow 20c) and thus the position of the end position 12a can be adjusted by the nozzle position adjusting mechanism 80.

The irradiating unit 30 includes a semiconductor laser element 32 that emits a laser beam having a predetermined wavelength (for example, beam having a wavelength of 488 nm) as irradiation light (excitation light) L0, and an optical fiber 31 that propagates the irradiation light L0 and emits the irradiation light onto the vicinity of the flow (sample flow) 11A of the sample liquid A flowing through the flow passage 14a. The optical fiber 31 is disposed so that the optical axis 31a thereof substantially lies on the X direction perpendicular to the Z direction. Although the irradiating unit 30 includes the optical fiber 31 in the embodiment, it is satisfactory if the irradiating unit has the optical axis substantially parallel to the X direction which is substantially perpendicular to the Z direction.

The transmitted light receiving unit 50 includes an optical fiber 51 and a light receiving element 52. The optical fiber 51 receives the transmitted light L1 from the specimen S near the sample flow 11A. The light receiving element 52 receives the transmitted light L1 propagated through the optical fiber 51, detects the transmitted light as a transmitted light signal SG1, and sends the detected transmitted light signal SG1 to the analyzing unit 90. For example, a photomultiplier, a photodetector, or the like is used as the light receiving element 52.

The optical fiber 51 is provided at a position directly facing the optical fiber 31 with the capillary portion 14 of the flow cell 12 interposed between the optical fibers. Here, the position directly facing the optical fiber is set so that a light receiving surface 51b of the optical fiber 51 perpendicular to the optical axis 51a faces an end face 31b of the optical fiber 31 perpendicular to the optical axis 31a and the optical axis 31a of the optical fiber 31 of the irradiating unit 30 is substantially parallel to the optical axis 51a of the optical fiber 51 of the transmitted light receiving unit 50.

It is preferable to substantially align the optical axis 31a of the optical fiber 31 of the above-mentioned irradiating unit 30 with the optical axis 51a of the optical fiber 51 of the transmitted light receiving unit 50 by changing the position of the optical fiber 31 of the irradiating unit 30 in the Y direction (the direction of an arrow 21b) and the Z direction (the direction of an arrow 21c) by the irradiation position adjusting mechanism 70. Further, the optical fiber 51 is fixed to the flow cell 12.

Furthermore, the optical fiber 51 is provided so that the optical axis 51a passes through the substantial center O of the flow passage 14a of the capillary portion 14 substantially in the X direction substantially perpendicular to the Z direction and on a plane substantially perpendicular to the Z direction.

Although the transmitted light receiving unit 50 includes the optical fiber 51 in the embodiment, it is satisfactory if the transmitted light receiving unit may be configured such that the optical axis of the transmitted light receiving unit substantially lies on the X direction substantially perpendicular to the Z direction, the light receiving surface of the transmitted light receiving unit substantially perpendicular to the optical axis faces the irradiating unit 30, and the center of the light receiving surface of the transmitted light receiving unit is substantially aligned with the optical axis of the irradiating unit 30.

Further, in this case, the diameter d" of the light receiving surface of the transmitted light receiving unit 50 and the irradiation diameter D of the irradiation light L0 that is irradiated from the irradiating unit 30 onto the light receiving surface b of the transmitted light receiving unit 50 are set so as to satisfy the following Relational Expression (1).

[Expression 1]

$$d" \leq D \qquad (1)$$

When the transmitted light receiving unit 50 receives the transmitted light L1 so as to satisfy Relational Expression (1), an optimum positional relationship with the optical axis 31a of the irradiating unit 30 and the change of the transmitted light signal may be received with high sensitivity. Accordingly, it may be possible to increase the sensitivity of the transmitted light signal SG1 that is detected by the transmitted light receiving unit 50. Here, the irradiation diameter D is the diameter of a beam, and means the diameter corresponding to $1/e^2$ (=13.5%) of the intensity of a beam at the center of the beam.

When the transmitted light receiving unit 50 includes the optical fiber 51 as illustrated in FIGS. 1, 2, and 3, it is preferable that the core diameter d of a core 51*c* of the optical fiber 51 and the irradiation diameter D of the irradiation light L0 that is irradiated from the irradiating unit 30 onto the light receiving surface 51*b* of the optical fiber 51 be set so as to satisfy the following Relational expression (2).

[Expression 2]

$$d \leq D \tag{2}$$

When the optical fiber 51 of the transmitted light receiving unit 50 receives the transmitted light L1 so as to satisfy Relational expression (2), an optimum positional relationship with the optical axis 31*a* of the irradiating unit 30 and the change of the transmitted light signal may be received with high sensitivity. Accordingly, it may be possible to increase the sensitivity of the transmitted light signal SG1 that is detected by the light receiving element 52. Here, the core diameter d complies with JIS C 6820 (the general principle of an optical fiber).

Further, it is preferable that the clad diameter d' of a clad 51*d* of the optical fiber 51 and the outer irradiation diameter D' of the irradiation light L0 that is irradiated from the irradiating unit 30 onto the light receiving surface 51*b* of the optical fiber 51 be set so as to further satisfy the following Relational Expression (3).

[Expression 3]

$$D' \leq d' \tag{3}$$

When the optical fiber 51 of the transmitted light receiving unit 50 receives the transmitted light L1 so as to satisfy Relational Expression (3), an optimum positional relationship with the optical axis 31*a* of the irradiating unit 30 and the change of the transmitted light signal may be further received with higher sensitivity. Accordingly, it may be possible to increase the sensitivity of the transmitted light signal SG1 that is detected by the light receiving element 52. Further, it may be possible to prevent the irradiation light L0 from straying. Here, the clad diameter d' complies with JIS C 6820 (the general principle of an optical fiber). Furthermore, the outer irradiation diameter D' means the diameter corresponding to 5% of the intensity of a beam at the center of the beam.

The position of the optical fiber 31 of the irradiating unit 30 may be changed and adjusted in the X direction (the direction of an arrow 21*a*) by the irradiation position adjusting mechanism 70 so that Relational Expression (1) is satisfied, Relational Expression (2) is further satisfied, and Relational Expression (3) is still further satisfied.

The scattering/fluorescent light receiving unit 60 includes an optical fiber 61 and a light receiving element 62. The optical fiber 61 receives lateral scattering light and/or fluorescent light L2 from the specimen near the sample flow 11A. The light receiving element 62 receives the lateral scattering light and/or fluorescent light L2 propagated through the optical fiber 61, detects the lateral scattering light and/or fluorescent light as a scattering/fluorescent light signal SG2, and sends the detected scattering/fluorescent light signal SG2 to the analyzing unit 90. For example, a photomultiplier, a photodetector, or the like is used as the light receiving element 62. It is preferable that a plurality of light receiving elements 62 be provided and lateral scattering light and/or fluorescent light, which is separated for every wavelength by optical filters and the like, be received by the plurality of light receiving elements 62. In this case, the respective light receiving elements 62 detect different scattering/fluorescent light signals SG2, and the plurality of scattering/fluorescent light signals SG2 detected by the respective light receiving elements 62 are sent to the analyzing unit 90. Further, in FIGS. 1 to 3, the optical information analyzing device 10 has been provided with one scattering/fluorescent light receiving unit 60. However, the optical information analyzing device may be provided with a plurality of similar scattering/fluorescent light receiving units.

The optical fiber 61 is provided so that an optical axis 61*a* is substantially perpendicular to the optical axis 51*a* of the optical fiber 51 and the optical axis 31*a* of the optical fiber 31 (that is, substantially perpendicular to the X direction) and passes through the substantial center O of the flow passage 14*a* of the capillary portion 14 substantially in a Y direction, which is a direction substantially perpendicular to the Z direction, and on a plane perpendicular to the Z direction. Further, the optical fiber 61 is fixed to the flow cell 12. Meanwhile, the optical axis 61*a* of the scattering/fluorescent light receiving unit 60 is not necessarily perpendicular to the optical axis 51*a* or the optical axis 31*a*, and may intersect the optical axis 51*a* or the optical axis 31*a*.

Furthermore, the optical fibers 51 and 61 may be disposed so that the light receiving surfaces 51*b* and 61*b* directly come into contact with the sheath flow 11B.

The nozzle position adjusting mechanism 80 adjusts the position of the end portion 15*a* of the introduction nozzle 15 by moving the end portion 15*a* of the introduction nozzle 15 in the flow passage 13*a* of the flow cell 12 in the X direction (the direction of an arrow 20*a*), the Y direction (the direction of an arrow 20*b*), and the Z direction (the direction of an arrow 20*c*) so that the center of the sample flow 11A passes through a position where the optical axis 51*a* of the optical fiber 51, the optical axis 31*a* of the optical fiber 31, and the optical axis 61*a* of the optical fiber 61 intersect one another (a substantial center O of the flow passage 14*a* of the capillary portion 14 positioned on the plane perpendicular to the Z direction). That is, when the position of the end portion 15*a* of the introduction nozzle 15 is adjusted by the nozzle position adjusting mechanism 80, the position of the sample flow 11A in the flow passage 14*a* is adjusted to an optimum position in a measurement region that is the region of the transmitted light L1 (irradiation light L0) near the position (the substantial center O) where the optical axis 51*a* of the optical fiber 51, the optical axis 31*a* of the optical fiber 31, and the optical axis 61*a* of the optical fiber 61 intersect one another.

In this specification, the term "center O of the sample flow 11A" means a central position of a range through which the sample flow 11A passes, on the plane perpendicular to the flow direction (Z direction) of the sample flow 11A. Further, the term "position of the sample flow 11A in the flow passage 14*a*" means a position through which the center of the sample flow 11A passes, on the plane within the flow passage 14*a* that passes through the center O of the measurement region in the flow passage 14*a* and is perpendicular to the flow direction of the sample flow 11A (Z direction). Further, the measurement region is determined on the basis of the diameter of the irradiation light, which is irradiated from the irradiating unit, in the flow passage or the light receiving region of the transmitted light receiving unit or the scattering/fluorescent light receiving unit.

Furthermore, the term "optimum position" means a position where the transmitted light signal SG1 and the scattering/fluorescent light signal SG2 of the specimen S detected by the transmitted light receiving unit 50 and the scattering/fluorescent light receiving unit 60 can be detected with the highest sensitivity and the variation of the optical information on the specimen S measured on the basis of the detected transmitted light signal SG1 and the detected scattering/fluorescent light signal SG2 of the specimen S is the least. Accordingly, while irradiation light (excitation light) is actually irradiated onto the sample flow 11A in the flow passage 14a, the position of the sample flow 11A in the flow passage 14a is adjusted to the optimum position. That is, the center of the sample flow 11A is adjusted so as to be aligned with the position (the substantial center O) where the optical axis 51a of the optical fiber 51, the optical axis 31a of the optical fiber 31, and the optical axis 61a of the optical fiber 61 intersect one another.

Figure 4:
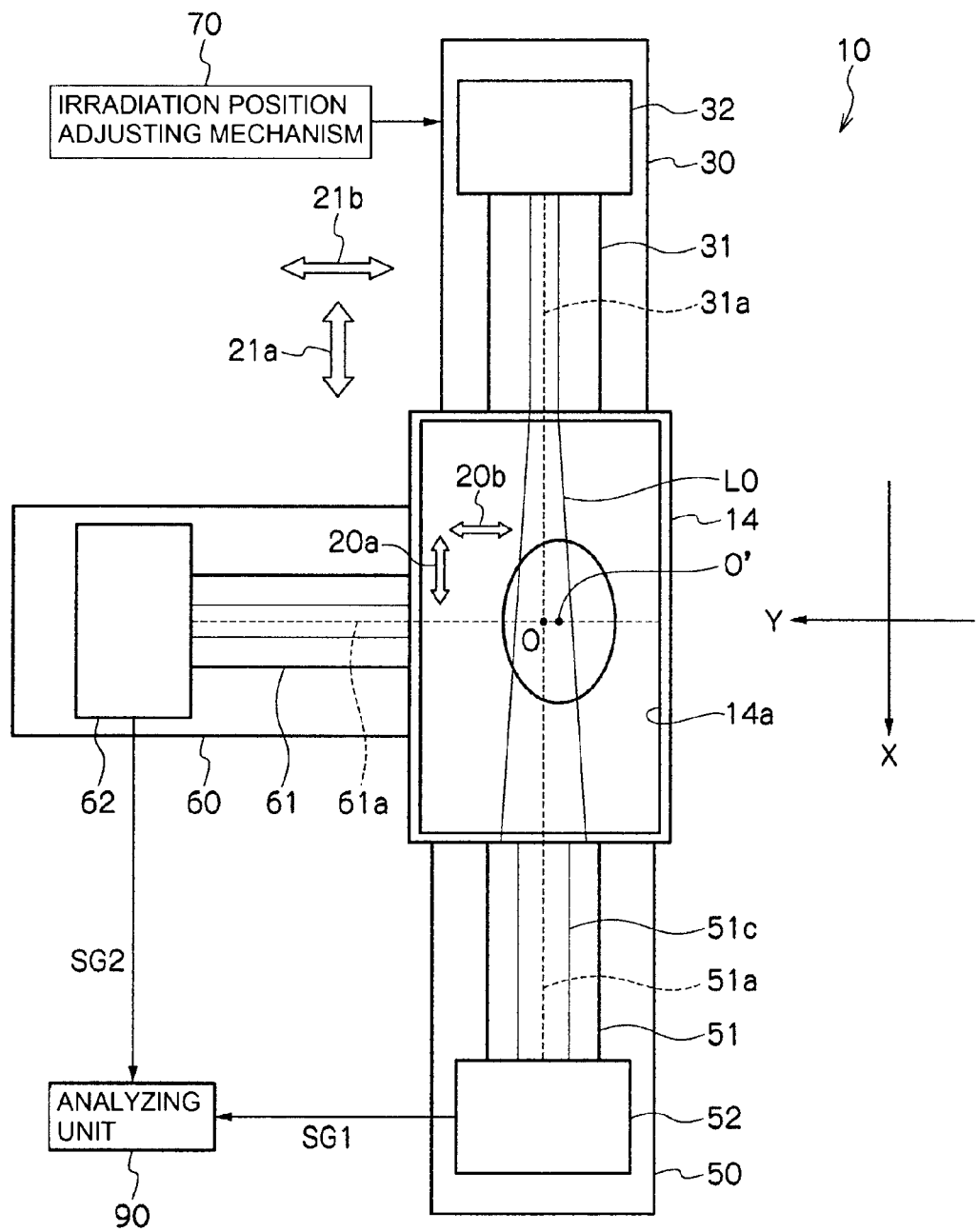
FIG. 4 is a view illustrating adjustment position in the case of the analysis of specimens S of which the light receiving efficiency of a fluorescent ingredient of a surface antibody had better be improved.

Meanwhile, in the above description, the optimum position of the above-mentioned sample flow 11A has been exemplified as the position (the substantial center O) where the optical axis 51a of the optical fiber 51, the optical axis 31a of the optical fiber 31, and the optical axis 61a of the optical fiber 61 intersect one another. However, in the case of a certain specimen S, for the improvement of the light receiving efficiency of a fluorescent ingredient of a surface antibody, the optimum position may be a position O' further distant from the light receiving surface 61b of the optical fiber 61 in the Y direction as compared to the position (the substantial center O) where the optical axis 51a of the optical fiber 51, the optical axis 31a of the optical fiber 31, and the optical axis 61a of the optical fiber 61 intersect one another, as illustrated in FIG. 4. In this case, the center of the sample flow 11A may be adjusted so as to be aligned with the position O'.

The analyzing unit 90 measures the optical information on specimens S on the basis of the transmitted light signal SG1 detected by the transmitted light receiving unit 50 and the scattering/fluorescent light signal SG2 detected by the scattering/fluorescent light receiving unit 60, and analyzes the specimens S on the basis of the measured optical information. Moreover, the analyzing unit 90 may send the result of the analysis of the specimens S to a dispensing unit (not illustrated), which dispenses specimens S, on the basis of the result of the analysis.

The optical information analyzing device 10 according to the embodiment of the invention illustrated in FIGS. 1 to 3 has included the scattering/fluorescent light receiving unit 60. However, the optical information analyzing device may not include the scattering/fluorescent light receiving unit 60.

It may be possible to increase the sensitivity of the transmitted light signal SG1, which is detected by the transmitted light receiving unit 50, by the above-mentioned optical information analyzing device 10 according to the embodiment of the invention. Further, it may be possible to increase the sensitivity of the scattering/fluorescent light signal SG2 that is detected by the scattering/fluorescent light receiving unit 60. Furthermore, it may be possible to measure the optical information on the specimens S with a small variation by the analyzing unit 90 on the basis of the transmitted light signal SG1 and the scattering/fluorescent light signal SG2 that are detected by the transmitted light receiving unit 50 and the scattering/fluorescent light receiving unit 60. Moreover, in the case of a certain specimen S, it may also be possible to improve the light receiving efficiency of a fluorescent ingredient of a surface antibody.

Next, a sequence of processing for analyzing the optical information on specimens S using the optical information analyzing device 10 according to the embodiment of the invention illustrated in FIGS. 1 to 3 will be briefly described.

Figure 5:
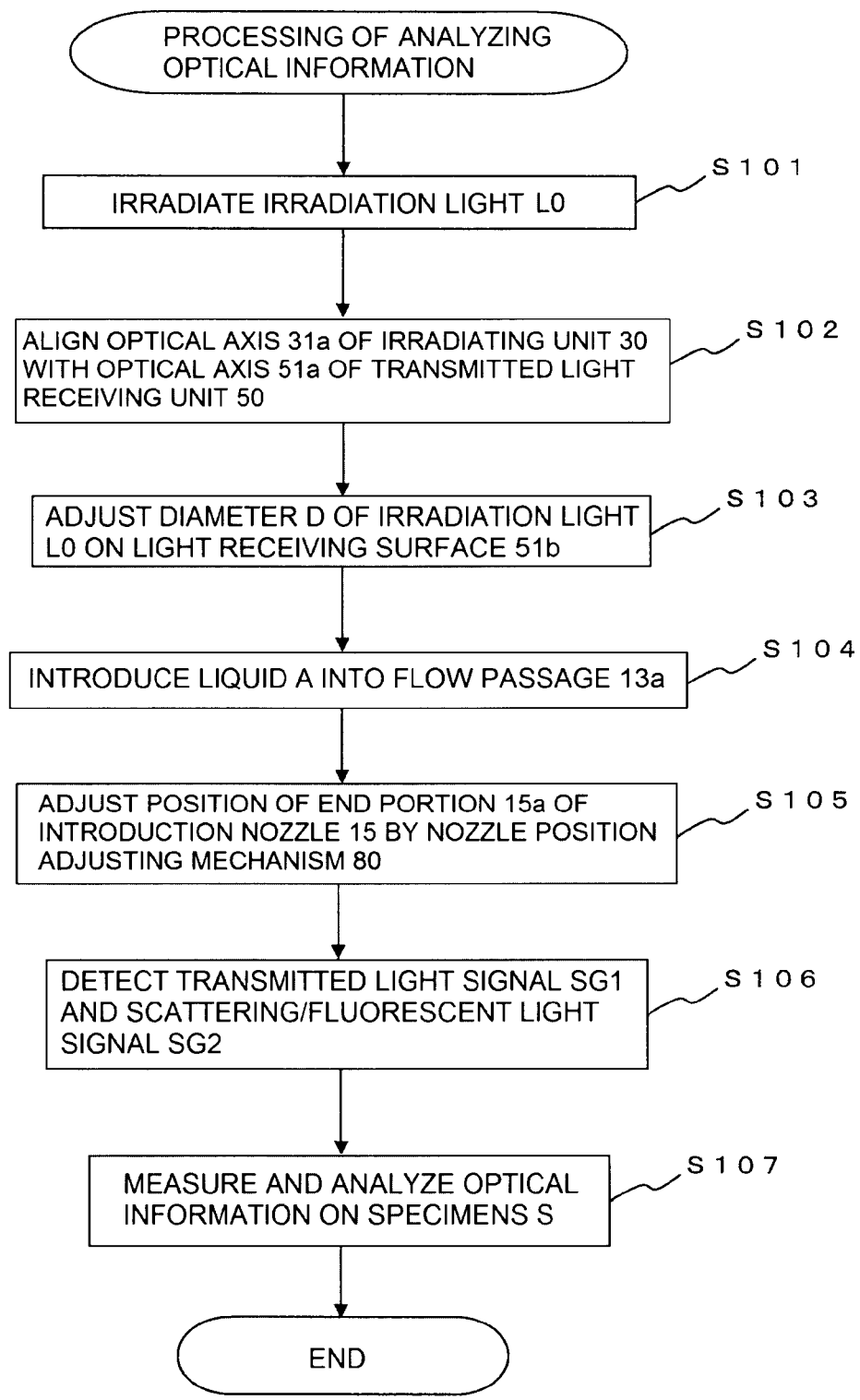
FIG. 5 is a flowchart illustrating a sequence of processing for analyzing the optical information on specimens S using the optical information analyzing device 10 according to the embodiment of the invention illustrated in FIGS. 1 to 3.

FIG. 5 is a flowchart illustrating a sequence of processing for analyzing the optical information on specimens S using the optical information analyzing device 10 according to the embodiment of the invention illustrated in FIGS. 1 to 3.

As illustrated in FIG. 5, first, the capillary portion 14 of the flow cell 12 is exposed to the irradiation light L0 from the irradiating unit 30 (step 1: S101), and adjustment is performed such that the optical axis 31a of the optical fiber 31 of the irradiating unit 30 is aligned with the optical axis 51a of the optical fiber 51 of the transmitted light receiving unit 50 fixed to the flow cell 12 by changing the position of the optical fiber 31 of the irradiating unit 30 in the Y direction and the Z direction with the irradiation position adjusting mechanism 70 (step 2: S102). Further, the optical information analyzing device may adjust the position of the optical fiber 31 of the irradiating unit 30 with the irradiation position adjusting mechanism 70 so that the optical axis 31a of the optical fiber 31 and the optical axis 61a of the optical fiber 61 intersect each other at the substantial center O (see FIG. 4). That is, the optical information analyzing device may perform adjustment so as to align the substantial center of a second measurement region of the scattering/fluorescent light receiving unit 60 with the substantial center of the measurement region of the transmitted light receiving unit 50.

Meanwhile, the optical axis 51a of the optical fiber 51 of the transmitted light receiving unit 50 passes through the substantial center O of the flow passage 14a of the capillary portion 14, and is positioned with high accuracy so as to be parallel to the X direction and perpendicular to the Z direction (see FIGS. 1 and 3). Moreover, a position where the optical axis 51a of the optical fiber 51 of the transmitted light receiving unit 50 is substantially aligned with the optical axis 31a of the optical fiber 31 of the irradiating unit 30 means a position where the amount of irradiation light irradiated from the irradiating unit 30 and received by the transmitted light receiving unit 50 becomes maximum. Further, it is preferable that the adjustment of the position of the optical fiber 31 of the irradiating unit 30 be performed while the sheath liquid B or the sample liquid A flows through the flow passage 14a of the capillary portion 14.

Next, the position of the optical fiber 31 of the irradiating unit 30 is changed in the X direction by the irradiation position adjusting mechanism 90 so that adjustment is performed to satisfy Relational Expression (1) (step 3: S103). Here, when the irradiating unit 30 irradiates light using a lens but without using the optical fiber 31, the adjustment to satisfy Relational Expression (1) is performed by substantially aligning the center of an irradiation region, which is determined by the lens, with the center O of the flow passage 14a of the capillary portion 14. Furthermore, it is preferable that adjustment be performed in the step 3 so as to satisfy Relational Expression (2). Moreover, it is preferable that adjustment be performed in the step 3 so as to further satisfy Relational Expression (3).

Next, the sample liquid A, which is adjusted so that the relative positions of the specimens S with respect to the irradiation light L0 irradiated from the irradiating unit 30 change at the constant speed, is introduced, from a specimen storage portion (not illustrated), into the flow passage 13a of the flow cell 12 through the introduction nozzle 15 as the sample flow 11A (step 4: S104). Meanwhile, the processing timing of the step 4 of introducing the sample liquid A into the flow passage 13a of the flow cell 12 through the introduction nozzle 15 is not limited to the timing illustrated in the flowchart. For example, the processing timing may be set before the step 1. That is, it may be set to any timing as long as the processing timing is set before the step 5 to be described below.

Next, the end portion 15a of the introduction nozzle 15 is moved in the flow passage 13a of the flow cell 12 in the X direction, the Y direction, and the Z direction by the nozzle position adjusting mechanism 80 to adjust the position of the end portion 15a of the introduction nozzle 15 so that the center of the sample flow 11A passes through the position (the center O) where the optical axis 51a of the optical fiber 51, the optical axis 31a of the optical fiber 31, and the optical axis 61a of the optical fiber 61 intersect one another (step 5: S105).

Meanwhile, the optical axis 61a of the optical fiber 61 of the scattering/fluorescent light receiving unit 60 passes through the substantial center O of the flow passage 14a of the capillary portion 14, and is positioned with high accuracy so as to be parallel to the Y direction and perpendicular to the Z direction (see FIGS. 2 and 3). Further, when the scattering/fluorescent light receiving unit 60 receives light using a lens but without using the optical fiber 61, the center of a scattering/fluorescent light receiving region, which is determined by the lens, is positioned so as to be substantially aligned with the center O of the flow passage 14a of the capillary portion 14.

Furthermore, as illustrated in FIG. 4, in the case of the analysis of specimens S of which the light receiving efficiency of a fluorescent ingredient of a surface antibody had better be improved, the end portion 15a of the introduction nozzle 15 is moved in the flow passage 13a of the flow cell 12 in the X direction, the Y direction, and the Z direction to adjust the position of the end portion 15a of the introduction nozzle 15 so that the center of the sample flow 11A passes through the position O', which is further distant from the light receiving surface 61b of the optical fiber 61 in the Y direction as compared to the position (the substantially center O) where the optical axis 51a of the optical fiber 51, the optical axis 31a of the optical fiber 31, and the optical axis 61a of the optical fiber 61 intersect one another.

Next, the transmitted light receiving unit 50 receives the transmitted light L1, detects the transmitted light as a transmitted light signal SG1, and sends the detected transmitted light signal SG1 to the analyzing unit 90; and the scattering/fluorescent light receiving unit 60 receives lateral scattering light and/or fluorescent light L2, detects the received lateral scattering light and/or fluorescent light as a scattering/fluorescent light signal SG2, and sends the detected scattering/fluorescent light signal SG2 to the analyzing unit 90 (step 6: S106).

Finally, the analyzing unit 90 measures the optical information on the specimens S on the basis of the transmitted light signal SG1 and the scattering/fluorescent light signal SG2 and analyzes the specimens S on the basis of the measured optical information (step 7: S107). Then, the procedure for analyzing the optical information on specimens S using the optical information analyzing device 10 according to the embodiment of the invention illustrated in FIGS. 1 to 3 ends. Meanwhile, further processing of dispensing specimens S on the basis of the result of the analysis of the step 7 may be performed after the step 7. Further, the steps 1 to 5 do not need to be performed for every analysis (to perform the steps 6 and 7).

It may be possible to increase the sensitivity of the transmitted light signal SG1, which is detected by the transmitted light receiving unit 50, by the above-mentioned procedure for analyzing the optical information on specimens S illustrated in FIG. 5. Further, it may be possible to increase the sensitivity of the scattering/fluorescent light signal SG2 that is detected by the scattering/fluorescent light receiving unit 60. Furthermore, it may be possible to measure the optical information on the specimens S with a small variation by the analyzing unit 90 on the basis of the transmitted light signal SG1 and the scattering/fluorescent light signal SG2 that are detected by the transmitted light receiving unit 50 and the scattering/fluorescent light receiving unit 60. Moreover, in the case of a certain specimen S, it may also be possible to improve the light receiving efficiency of a fluorescent ingredient of a surface antibody.

Next, another optical information analyzing device 10 according to the embodiment of the invention will be described with reference to FIGS. 6 to 8.

Figure 6:
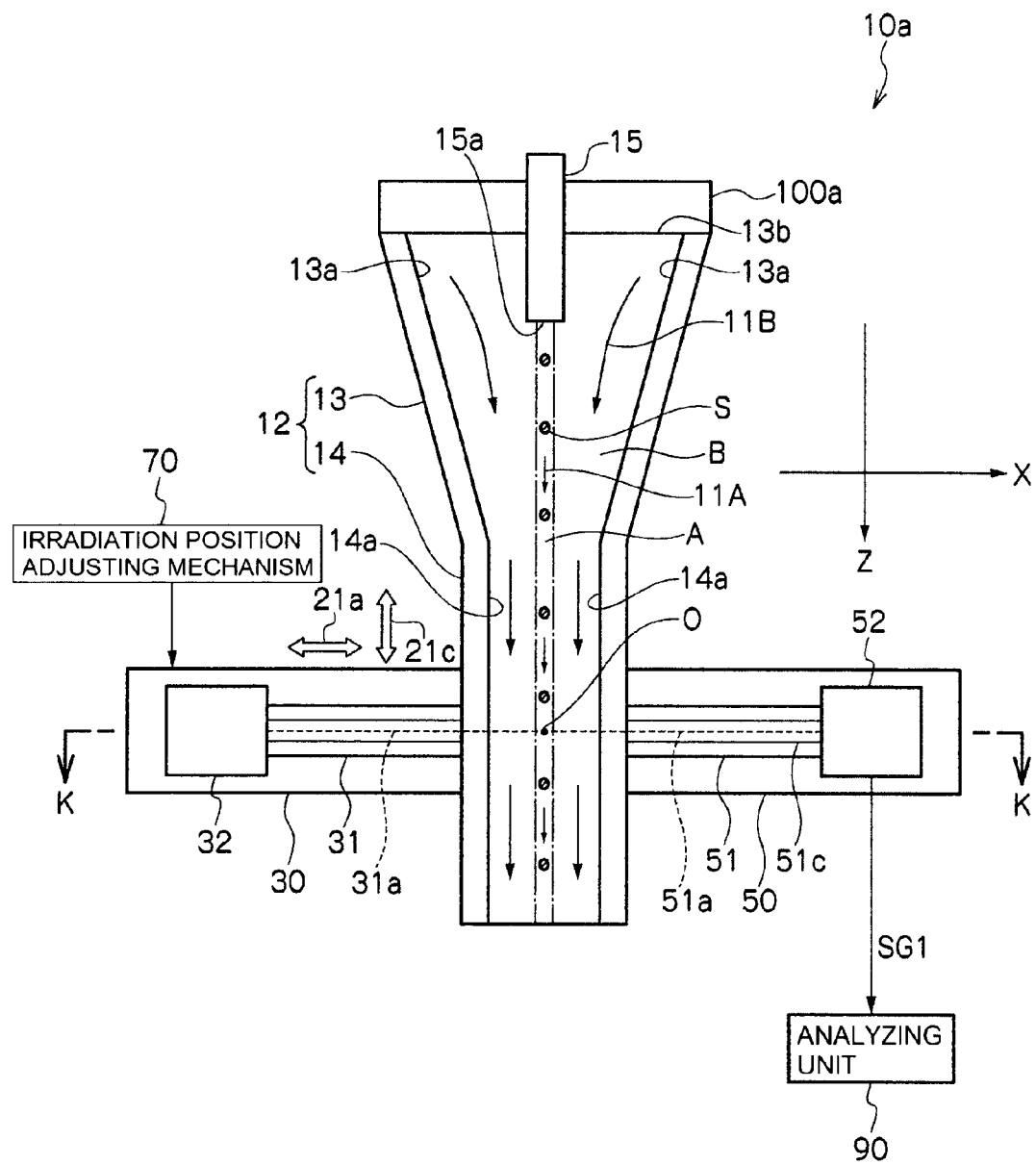
FIG. 6 is a schematic longitudinal sectional view of another optical information analyzing device according to the embodiment of the invention.
Figure 9:
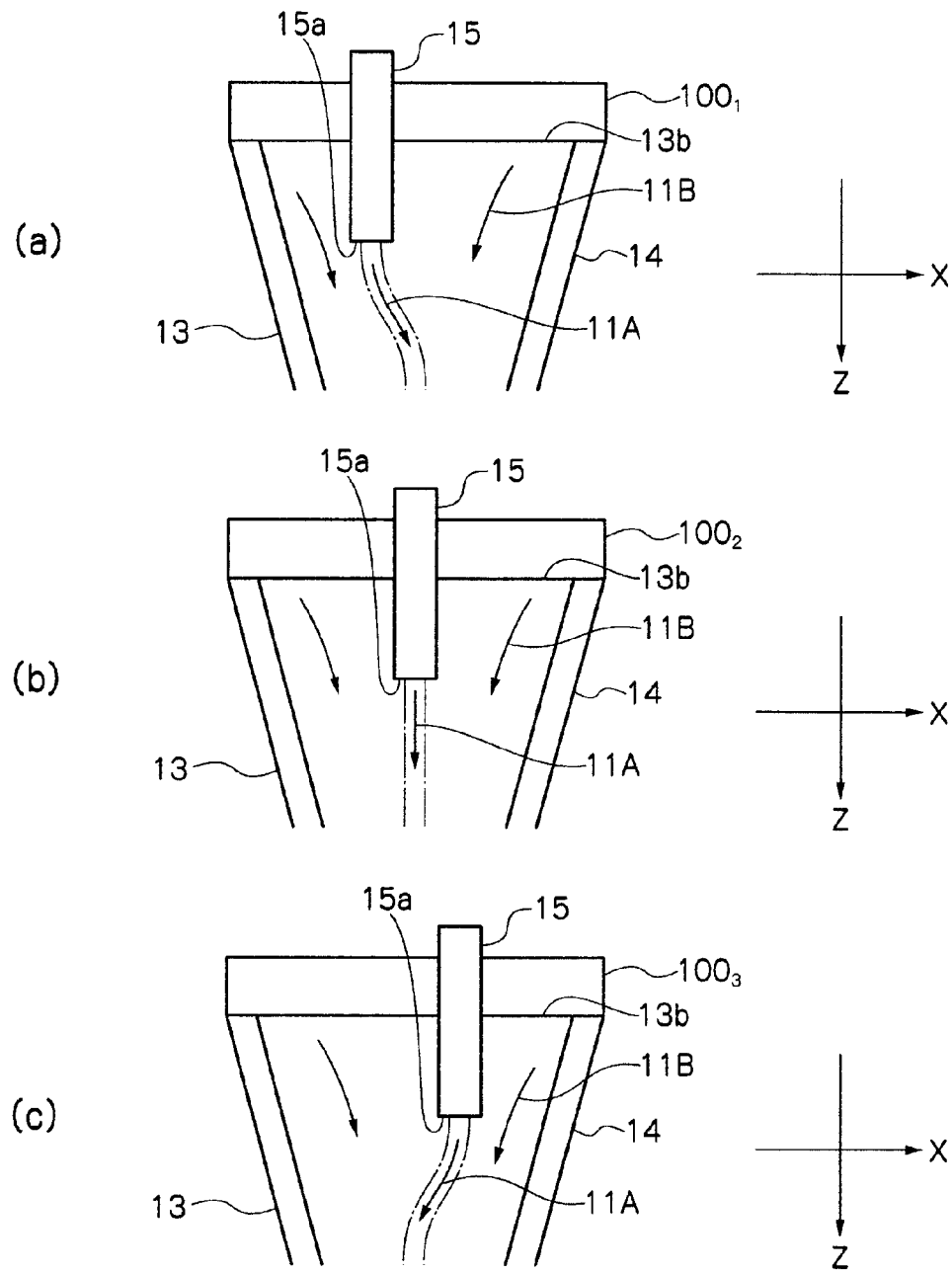
FIG. 9 is a view illustrating offset jigs.
Figure 10:
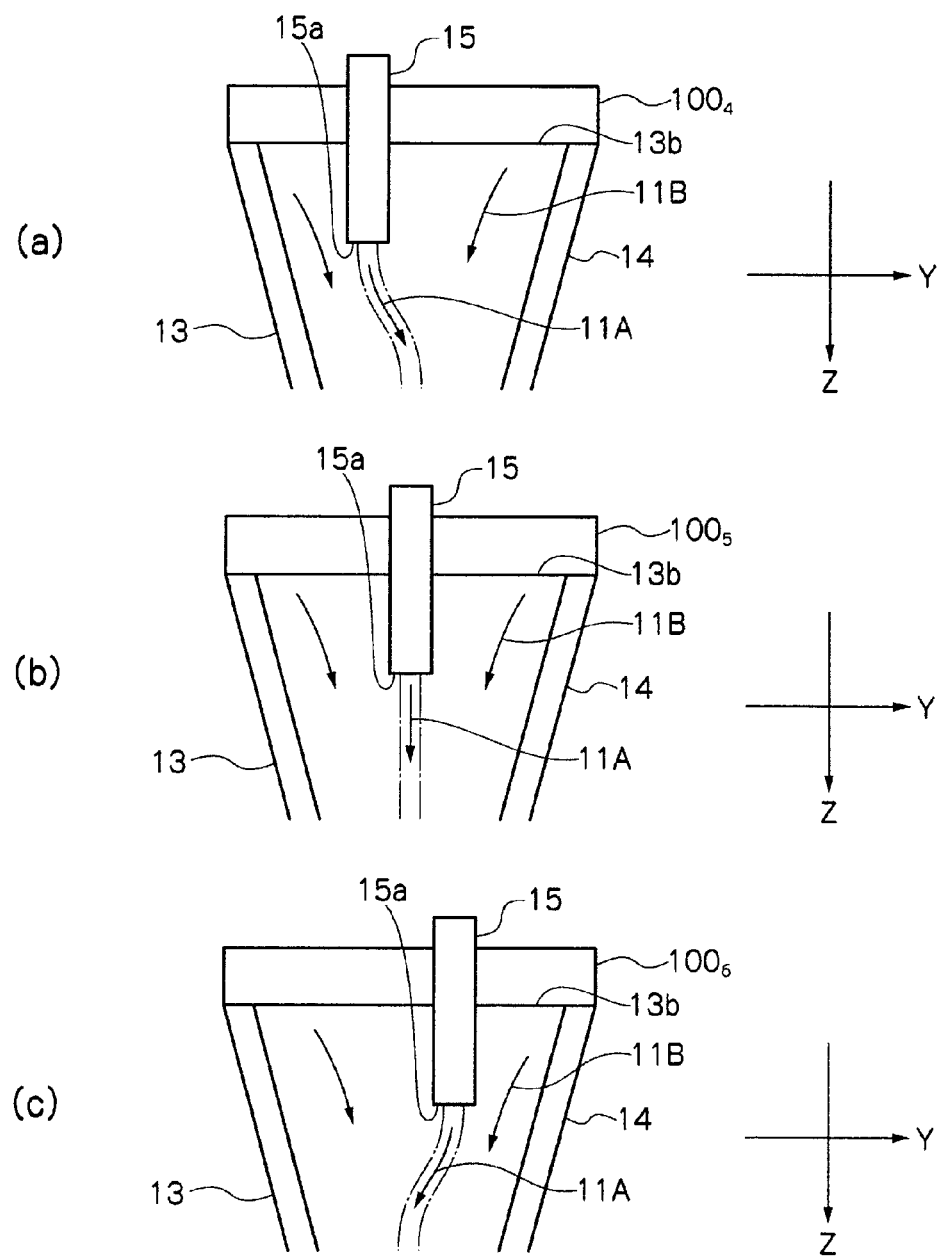
FIG. 10 is another view illustrating offset jigs.
Figure 11:
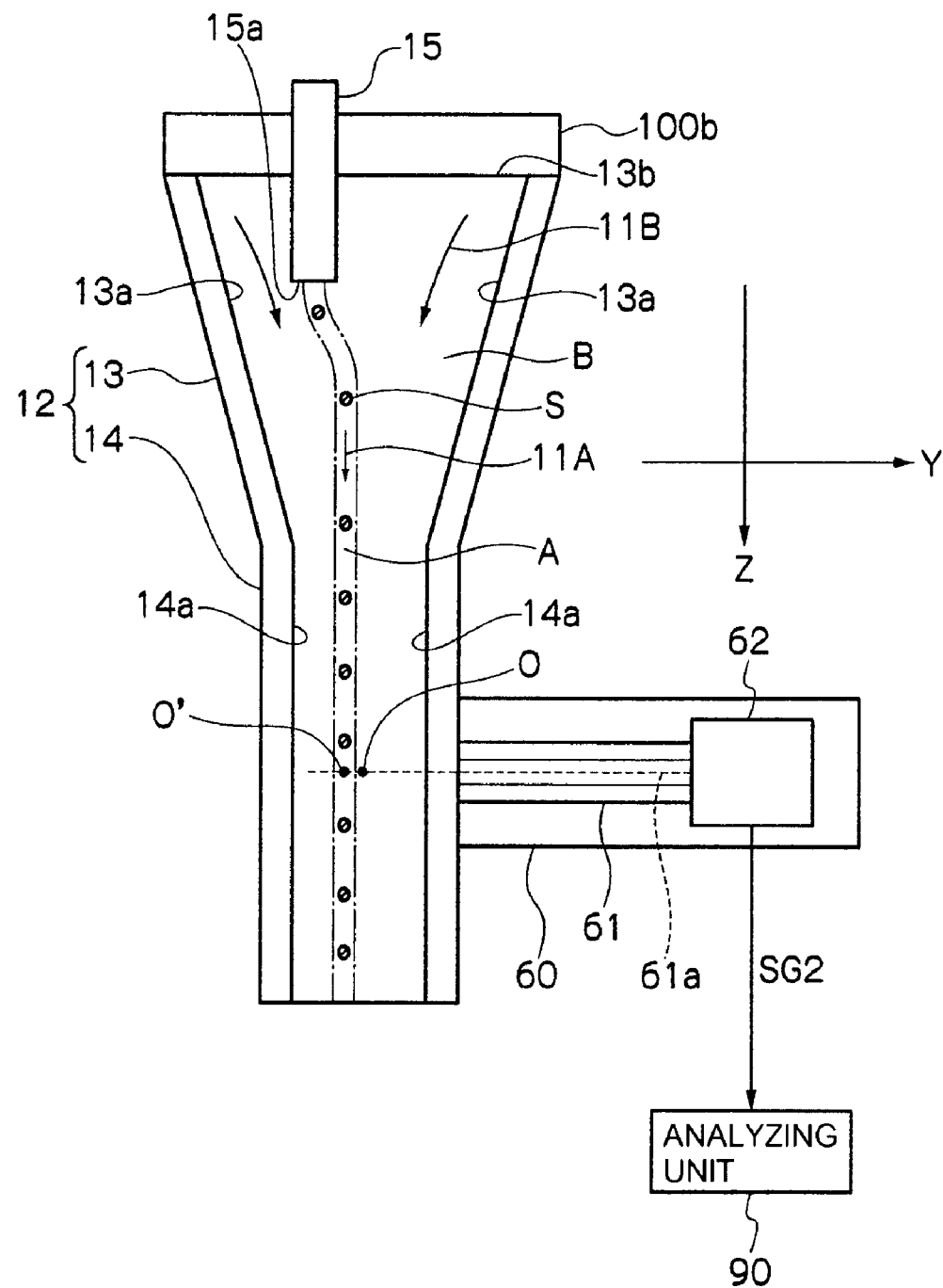
FIG. 11 is a view illustrating an optimum offset jig in the case of the analysis of specimens S of which the light receiving efficiency of a fluorescent ingredient of a surface antibody had better be improved.

FIG. 6 is a schematic longitudinal sectional view of another optical information analyzing device according to the embodiment of the invention. Further, FIG. 7 is a schematic longitudinal sectional view of the optical information analyzing device of FIG. 6 that is rotated about a Z axis by an angle of 90°. FIG. 8 is a schematic cross-sectional view of the optical information analyzing device of FIGS. 6 and 7 taken along the line K-K. Furthermore, FIGS. 9 to 11 are views illustrating offset jigs.

Figure 7:
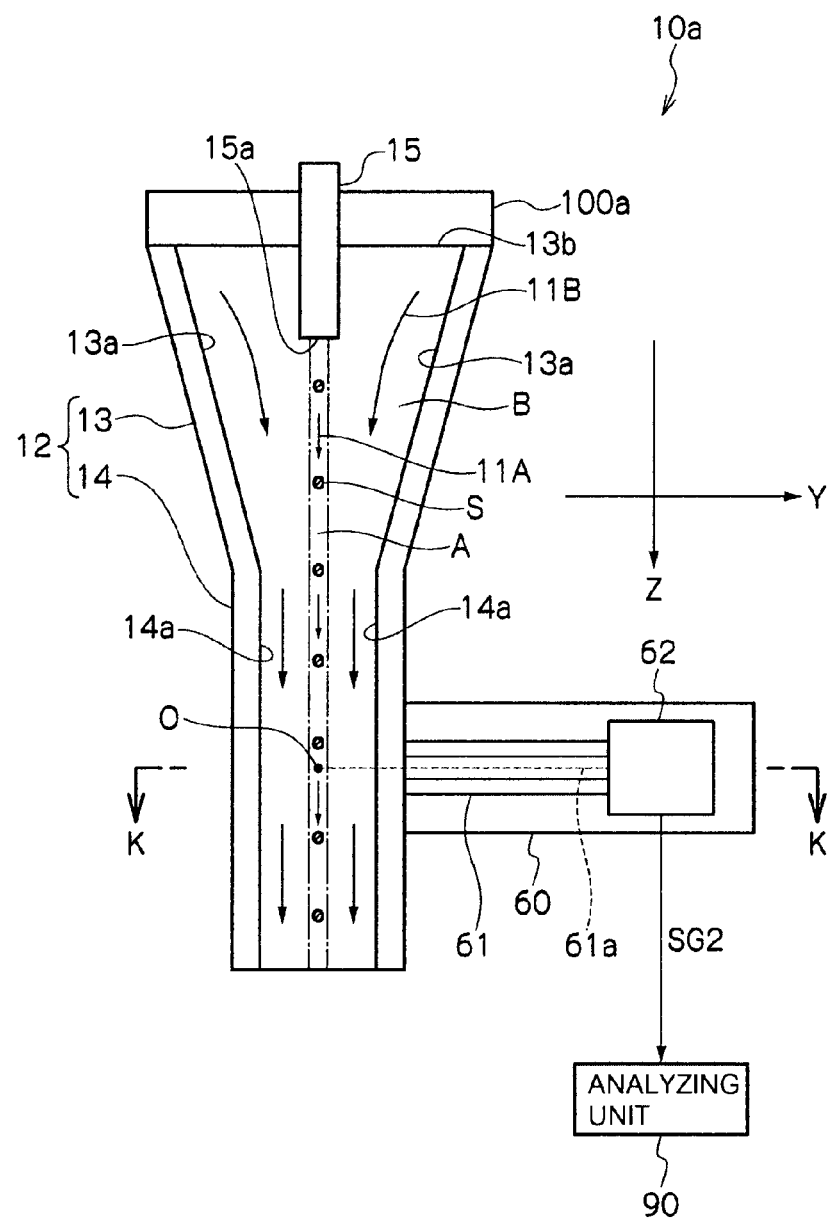
FIG. 7 is a schematic longitudinal sectional view of the optical information analyzing device of FIG. 6 that is rotated about a Z axis by an angle of 90°.
Figure 8:
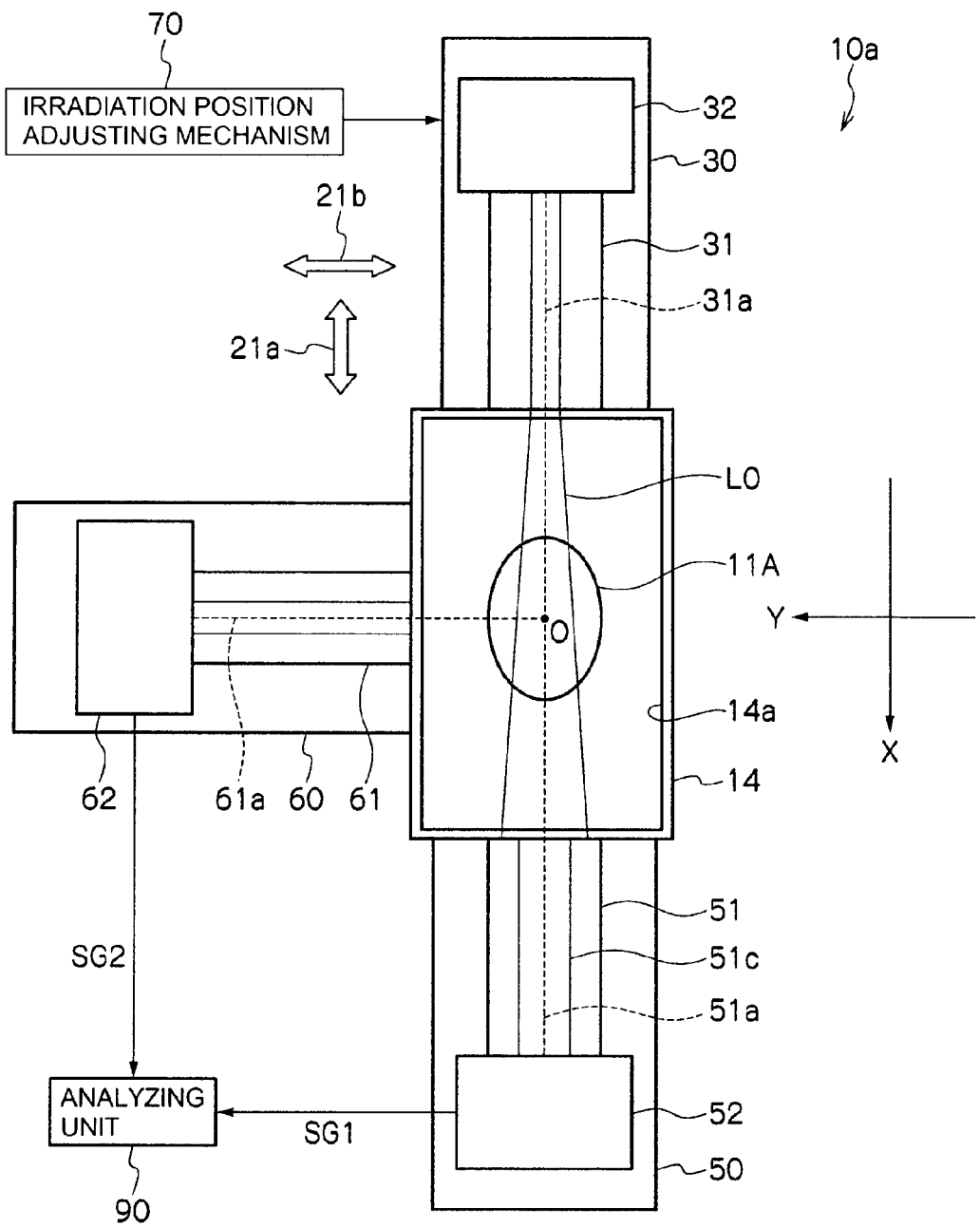
FIG. 8 is a schematic cross-sectional view of the optical information analyzing device of FIGS. 6 and 7 taken along the line K-K.

An optical information analyzing device 10a according to the embodiment of the invention illustrated in FIGS. 6 to 8 is different from the optical information analyzing device 10 according to the embodiment of the invention illustrated in FIGS. 1 to 3 in that, in place of the nozzle position adjusting mechanism 80 for adjusting the position of the end portion 15a of the introduction nozzle 15 so as to be aligned with the transmitted light receiving unit 50 and the irradiating unit 30, a plurality of offset jigs $100_i$ (i=1 to n) for adjusting the position of the end portion 15a of the introduction nozzle 15 so as to be aligned with the transmitted light receiving unit 50 and the irradiating unit 30 is provided, an optimum offset jig $100_a$ is selected among the offset jigs $100_i$ (i=1 to n), and an introduction nozzle 15 is mounted on the selected offset jig $100_a$, and the selected offset jig is fixed to an upper end 13b of the tapered portion 13 of the flow cell 12.

For example, as illustrated in FIGS. 9(a) to 9(c) and FIGS. 10(a) to 10(c), the introduction nozzle 15 is mounted on any one of the offset jigs $100_i$ (i=1 to n) and the offset jig is fixed to the upper end 13b of the tapered portion 13 of the flow cell 12, so that the position of the end portion 15a of the introduction nozzle 15 is adjusted. That is, an optimum offset jig $100_a$ is selected among the plurality of offset jigs $100_i$ (i=1 to n), and the optical information on the specimens S is measured using the selected optimum offset jig $100_a$. The optimum offset jig $100_a$ allows the center of the sample flow 11A to pass through the position (the center O) where the optical axis 51a of the optical fiber 51, the optical axis 31a of the optical fiber 31, and the optical axis 61a of the optical fiber 61 intersect one another when the introduction nozzle 15 is mounted on the offset jig and the offset jig is fixed to the upper end 13b of the tapered portion 13 of the flow cell 12 as illustrated in FIG. 8.

Further, in the case of the analysis of specimens S of which the light receiving efficiency of a fluorescent ingredient of a surface antibody had better be improved, an optimum offset jig $100_b$ is selected among the plurality of offset jigs $100_i$ (i=1 to n), and the optical information on the specimens S is measured using the selected optimum offset jig $100_b$. The optimum offset jig $100_b$ allows the center of the sample flow 11A to pass through a position O' further distant from the light receiving surface 61b of the optical fiber 61 in the Y direction as compared to the position (the center O) where the optical axis 51a of the optical fiber 51, the optical axis 31a of the optical fiber 31, and the optical axis 61a of the optical fiber 61 intersect one another when the introduction nozzle 15 is mounted on the offset jig and the offset jig is fixed to the upper end 13b of the tapered portion 13 of the flow cell 12 as illustrated in FIG. 11.

Meanwhile, the selection of the optimum offset jig $100_a$ or the optimum offset jig $100_b$ is determined depending on the position of the actual sample flow 11A when the introduction nozzle 15 is mounted on each of the various offset jigs 100$_i$ (i=1 to n) and each of the various offset jigs is fixed to the upper end 13b of the tapered portion 13 of the flow cell 12.

It may be possible to increase the sensitivity of the transmitted light signal SG1, which is detected by the transmitted light receiving unit 50, by the above-mentioned optical information analyzing device 10a according to the embodiment of the invention. Further, it may be possible to increase the sensitivity of the scattering/fluorescent light signal SG2 that is detected by the scattering/fluorescent light receiving unit 60. Furthermore, it may be possible to measure the optical information on the specimens S with a small variation by the analyzing unit 90 on the basis of the transmitted light signal SG1 and the scattering/fluorescent light signal SG2 that are detected by the transmitted light receiving unit 50 and the scattering/fluorescent light receiving unit 60. Moreover, in the case of a certain specimen S, it may also be possible to improve the light receiving efficiency of a fluorescent ingredient of a surface antibody.

Next, a sequence of processing for analyzing the optical information on specimens S using the optical information analyzing device 10a according to the embodiment of the invention illustrated in FIGS. 6 to 8 will be briefly described.

Figure 12:
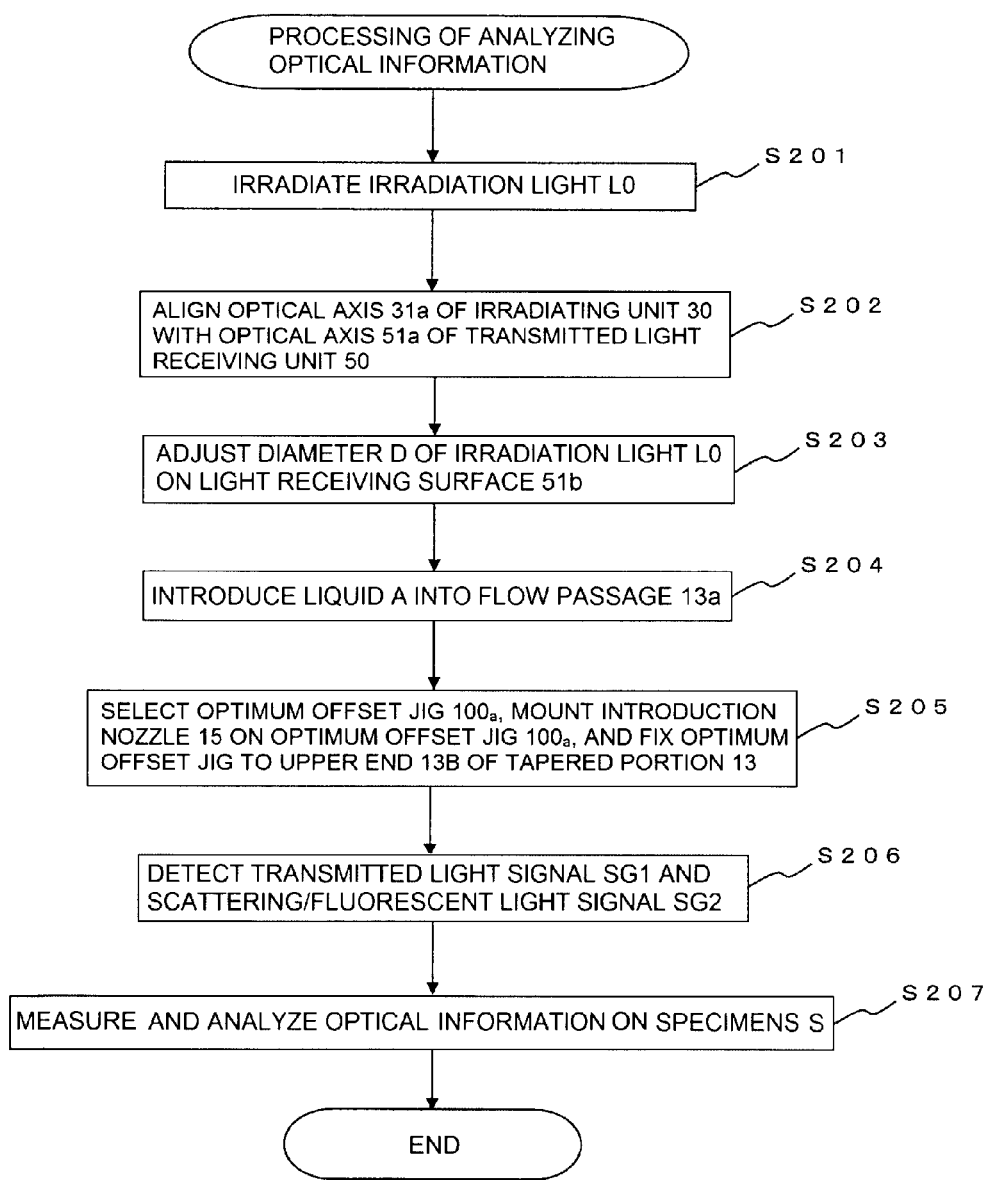
FIG. 12 is a flowchart illustrating a sequence of processing for analyzing the optical information on specimens S using another optical information analyzing device 10a according to the embodiment of the invention illustrated in FIGS. 6 to 8.

FIG. 12 is a flowchart illustrating a sequence of processing for analyzing the optical information on specimens S using the optical information analyzing device 10a according to the embodiment of the invention illustrated in FIGS. 6 to 8.

The sequence of processing, which is illustrated in FIG. 12, for analyzing the optical information on specimens S using the optical information analyzing device 10a according to the embodiment of the invention illustrated in FIGS. 6 to 8 is different from the sequence of processing, which is illustrated in FIG. 5, for analyzing the optical information on specimens S using the optical information analyzing device 10 according to the embodiment of the invention illustrated in FIGS. 1 to 3 in that, instead of adjusting the position of the end portion 15a of the introduction nozzle 15 by the nozzle position adjusting mechanism 80 in the step 5, an optimum offset jig 100$_a$ (which allows the center of the sample flow 11A to pass through the position (the substantial center O) where the optical axis 51a of the optical fiber 51, the optical axis 31a of the optical fiber 31, and the optical axis 61a of the optical fiber 61 intersect one another when the introduction nozzle 15 is mounted on the offset jig and the offset jig is fixed to the upper end 13b of the tapered portion 13 of the flow cell 12) is selected among the plurality of offset jigs 100$_i$ (i=1 to n), the introduction nozzle 15 is mounted on the selected offset jig 100$_a$, and the selected optimum offset jig is fixed to the upper end 13b of the tapered portion 13 of the flow cell 12.

Further, in the case of the analysis of specimens S of which the light receiving efficiency of a fluorescent ingredient of a surface antibody had better be improved, an optimum offset jig 100$_b$ is selected among the plurality of offset jigs 100$_i$ (i=1 to n), and the optical information on the specimens S is measured using the selected optimum offset jig 100$_b$. The optimum offset jig 100$_b$ allows the center of the sample flow 11A to pass through a position O' further distant from the light receiving surface 61b of the optical fiber 61 in the Y direction as compared to the position (the substantial center O) where the optical axis 51a of the optical fiber 51, the optical axis 31a of the optical fiber 31, and the optical axis 61a of the optical fiber 61 intersect one another when the introduction nozzle 15 is mounted on the offset jig and the offset jig is fixed to the upper end 13b of the tapered portion 13 of the flow cell 12 as illustrated in FIG. 11.

Meanwhile, the selection of the optimum offset jig 100$_a$ or the optimum offset jig 100$_b$ is determined depending on the position of the actual sample flow 11A when the introduction nozzle 15 is mounted on each of the various offset jigs 100$_i$ (i=1 to n) and each of the various offset jigs is fixed to the upper end 13b of the tapered portion 13 of the flow cell 12.

Meanwhile, the processing timing of the step 4 of introducing the sample liquid A into the flow passage 13a of the flow cell 12 through the introduction nozzle 15 is not limited to the timing illustrated in the flowchart. For example, the processing timing may be set before the step 1, or may be set to any timing as long as the processing timing is set before the step 5. Further, it is preferable that the adjustment of the position of the optical fiber 31 of the irradiating unit 30 in the step 2 be performed while the sheath liquid B or the sample liquid A flows through the flow passage 14a of the capillary portion 14. Furthermore, the steps 1 to 5 do not need to be performed for every analysis (to perform the steps 6 and 7).

It may be possible to increase the sensitivity of the transmitted light signal SG1, which is detected by the transmitted light receiving unit 50, by the above-mentioned sequence of processing for analyzing the optical information on specimens S illustrated in FIG. 12. Further, it may be possible to increase the sensitivity of the scattering/fluorescent light signal SG2 that is detected by the scattering/fluorescent light receiving unit 60. Furthermore, it may be possible to measure the optical information on the specimens S with a small variation by the analyzing unit 90 on the basis of the transmitted light signal SG1 and the scattering/fluorescent light signal SG2 that are detected by the transmitted light receiving unit 50 and the scattering/fluorescent light receiving unit 60. Moreover, in the case of a certain specimen S, it may also be possible to improve the light receiving efficiency of a fluorescent ingredient of a surface antibody.

The optical information analyzing device 10 illustrated in FIGS. 1 to 3, or the optical information analyzing device 10a illustrated in FIGS. 6 to 8 directly moves the end portion 15a of the introduction nozzle 15 so as to be aligned with the transmitted light receiving unit 50 and the irradiating unit 30 by the nozzle position adjusting mechanism 80 or the offset jig 100$_i$. The optical information analyzing device may include an adjustment unit for moving the flow cell 12, the scattering/fluorescent light receiving unit 60 and the transmitted light receiving unit 50 fixed to the flow cell 12, and the irradiating unit 30 of which the position is adjusted with respect to the transmitted light receiving unit 50, relative to the position of the end portion 15a of the introduction nozzle 15 so that the position of the end portion 15a of the introduction nozzle 15 is relatively moved so as to be aligned with the transmitted light receiving unit 50 and the irradiating unit 30.

The optical information analyzing device and the optical information analyzing method according to the embodiment of the invention may be applied to all fields including fields that require examination, analysis, and assay on biological macromolecules of sugars, amino acids, proteins, immune systems, and genes, for example, an engineering field, general agriculture about foods, agriculture, and seafood processing, a pharmaceutical field, medical fields about hygiene, health, immunity, epidemic, and heredity, and scientific fields about chemistry or biology.

Explanations of Letters or Numerals 10, 10a: optical information analyzing device
11A: sample flow
11B: sheath flow
12: flow cell
13: tapered portion
13a, 14a: flow passage 14: capillary portion
15: introduction nozzle
30: irradiating unit
31, 51, 61: optical fiber
50: transmitted light receiving unit
60: scattering/fluorescent light receiving unit
70: irradiation position adjusting mechanism
80: nozzle position adjusting mechanism
90: analyzing unit
$100_i$ (i=1 to n): offset jig
S: specimen
L0: irradiation light
L1: transmitted light
L2: lateral scattering light and/or fluorescent light
SG1: transmitted light signal
SG2: scattering/fluorescent light signal

The invention claimed is:

1. An optical information analyzing device that measures optical information on specimens by irradiating single-mode irradiation light to the specimens, which are objects to be measured and are dispersed in a liquid flowing through a flow passage, the optical information analyzing device comprising:
a flow cell that includes the flow passage;
an introduction nozzle that introduces the liquid into the flow passage of the flow cell;
an irradiating unit that irradiates irradiation light to the liquid flowing through the flow passage of the flow cell;
a transmitted light receiving unit that is provided at a position directly facing the irradiating unit, with the flow cell interposed therebetween, receives transmitted light, which is the irradiation light irradiated from the irradiating unit and transmitted through the liquid, and detects the transmitted light as a transmitted light signal; and
an analyzing unit that measures the optical information on the specimens on the basis of the transmitted light signal detected by the transmitted light receiving unit and analyzes the specimens,
wherein the transmitted light receiving unit is disposed so that a light receiving surface substantially perpendicular to an optical axis faces the irradiating unit and the center of the light receiving surface is substantially aligned with an optical axis of the irradiating unit,
wherein a diameter d" of the light receiving surface of the transmitted light receiving unit and an irradiation diameter D of the irradiation light that is irradiated from the irradiating unit onto the light receiving surface of the transmitted light receiving unit satisfy a relational expression of "d"≦D",
wherein the transmitted light receiving unit includes an optical fiber that is disposed so that a light receiving surface substantially perpendicular to the optical axis faces the irradiating unit,
wherein a core diameter d of the optical fiber and an irradiation diameter D of the irradiation light that is irradiated from the irradiating unit onto the light receiving surface of the optical fiber satisfy a relational expression of "d≦D", and
wherein a clad diameter d' of the optical fiber and an outer irradiation diameter D' of the irradiation light that is irradiated from the irradiating unit onto the light receiving surface of the optical fiber further satisfy a relational expression of "D'≦d'".

2. The optical information analyzing device according to claim 1, further comprising:
an adjustment unit that adjusts a position of a sample flow, which is generated by the liquid in the flow passage, relative to a measurement region in the flow passage that is determined on the basis of structure of the irradiating unit and the transmitted light receiving unit.

3. The optical information analyzing device according to claim 1, further comprising:
one or more scattering/fluorescent light receiving units which are provided at positions not directly facing the irradiating unit, have optical axes intersecting the optical axis of the irradiating unit, receive lateral scattering light and/or fluorescent light that are the irradiation light irradiated from the irradiating unit and emitted from the specimens, and detect the receive lateral scattering light and/or fluorescent light as a scattering/fluorescent light signal.

4. The optical information analyzing device according to claim 3,
wherein each of the scattering/fluorescent light receiving units includes an optical fiber that is disposed so that a light receiving surface substantially perpendicular to the optical axis does not face the irradiating unit.

5. The optical information analyzing device according to claim 3 or 4,
wherein the optical axis of the irradiating unit and the optical axis of each of the scattering/fluorescent light receiving units are substantially perpendicular to each other.

6. The optical information analyzing device according to claim 2,
wherein the position of the sample flow in the flow passage is adjusted relatively so that a substantial center of the sample flow passes through a substantial center of the measurement region.

7. The optical information analyzing device according to any one of claims 3 to 4,
wherein an adjustment unit relatively adjusts the position of the sample flow in the flow passage so that an substantial center of the sample flow intersects the optical axis of at least desired one of the scattering/fluorescent light receiving units and passes through a position distant from the scattering/fluorescent light receiving unit of which the optical axis intersects the substantial center of the sample flow as compared to a substantial center of a measurement region.

8. The optical information analyzing device according to claim 2,
wherein the adjustment unit includes a nozzle position adjusting mechanism that adjusts the position of an end portion of the introduction nozzle in the flow passage of the flow cell, and
the position of the end portion of the introduction nozzle in the flow passage of the flow cell is adjusted by the nozzle position adjusting mechanism, so that the position of the sample flow is adjusted relative to the measurement region.

9. The optical information analyzing device according to claim 2,
wherein the adjustment unit includes a plurality of offset jigs where the introduction nozzle is mounted and the position of an end portion of the introduction nozzle varies and which adjusts the position of the end portion of the introduction nozzle in the flow passage of the flow cell by being fixed to the flow cell, and
the position of the end portion of the introduction nozzle in the flow passage is adjusted so that the sample flow is positioned at a desired position relative to the measurement region, by an optimum offset jig selected among the plurality of offset jigs.

10. The optical information analyzing device according to any one of claims 1 or 2 to 4,
wherein the irradiating unit includes an optical fiber that propagates the irradiation light.

11. The optical information analyzing device according to any one of claims 1 or 2 to 4, further comprising:
an irradiation position adjusting mechanism that adjusts the direction and position of the optical axis of the irradiating unit and adjusts a distance between the irradiating unit and the light receiving surface of the transmitted light receiving unit so that the relational expressions are satisfied.

12. An optical information analyzing method that measures optical information on specimens by introducing a liquid in which specimens, objects to be measured, are dispersed into a flow passage of a flow cell through an introduction nozzle and irradiating single-mode irradiation light onto the specimens, which are dispersed in the liquid flowing through the flow passage, the optical information analyzing method comprising:
(a) a step of substantially aligning an optical axis of a transmitted light receiving unit with an optical axis of an irradiating unit, the transmitted light receiving unit being provided at a position directly facing the irradiating unit with the flow cell interposed therebetween, receiving transmitted light, which is the irradiation light irradiated from the irradiating unit and transmitted through the liquid, and detecting the transmitted light as a transmitted light signal; and
(b) a step of performing adjustment so that a diameter d" of the light receiving surface of the transmitted light receiving unit and an irradiation diameter D of the irradiation light that is irradiated from the irradiating unit onto the light receiving surface of the transmitted light receiving unit satisfy a relational expression of "d"≦D",
wherein when the transmitted light receiving unit includes an optical fiber and is disposed so that a light receiving surface substantially perpendicular to an optical axis of the fiber faces the irradiating unit, adjustment is performed in the step (b) so that a core diameter d of the optical fiber and an irradiation diameter D of the irradiation light that is irradiated from the irradiating unit onto the light receiving surface of the optical fiber satisfy a relational expression of "d≦D", and
wherein adjustment is performed in the step (b) so that a clad diameter d' of the optical fiber and an outer irradiation diameter D' of the irradiation light that is irradiated from the irradiating unit onto the light receiving surface of the optical fiber further satisfy a relational expression of "D'≦d'".

13. The optical information analyzing method according to claim 12, further comprising:
(c) a step of adjusting the position of a sample flow, which is generated by the liquid in the flow passage, relative to a measurement region in the flow passage that is determined on the basis of structure of the irradiating unit and the transmitted light receiving unit, after the step (b).

14. The optical information analyzing method according to claim 13,
wherein the step (c) relatively adjusts the position of the sample flow in the flow passage so that a substantial center of the sample flow passes through a substantial center of the measurement region.

15. The optical information analyzing method according to claim 13, further comprising:
(d) a step of receiving lateral scattering light and/or fluorescent light, which are the irradiation light irradiated from the irradiating unit and emitted from the specimens, and detecting the receive lateral scattering light and/or fluorescent light as a scattering/fluorescent light signal, and aligning the substantial center of the measurement region with a substantial center of a second measurement region determined on the basis of the structure of one or more scattering/fluorescent light receiving units that are provided at positions not directly facing the irradiating unit, before the step (c),
wherein the step (c) relatively adjusts the position of the sample flow in the flow passage so that a substantial center of the sample flow passes through a substantial center of the measurement region.

16. The optical information analyzing method according to claim 13, further comprising:
(d) a step of receiving lateral scattering light and/or fluorescent light, which are the irradiation light irradiated from the irradiating unit and emitted from the specimens, and detecting the receive lateral scattering light and/or fluorescent light as a scattering/fluorescent light signal, and aligning the substantial center of the measurement region with a substantial center of a second measurement region determined on the basis of the structure of one or more scattering/fluorescent light receiving units that are provided at positions not directly facing the irradiating unit, before the step (c),
wherein the step (c) relatively adjusts the position of the sample flow in the flow passage so that a substantial center of the sample flow intersects the optical axis of at least desired one of the scattering/fluorescent light receiving units and passes through a position distant from the scattering/fluorescent light receiving unit of which the optical axis intersects the substantial center of the sample flow as compared to the substantial center of the measurement region.

17. The optical information analyzing method according to claim 15 or 16,
wherein the step (d) makes the optical axis of the scattering/fluorescent light receiving unit and the optical axis of the irradiating unit be substantially perpendicular to each other in the measurement region.

18. The optical information analyzing method according to any one of claims 13 to 16,
wherein the step (c) adjusts the position of the sample flow relative to the measurement region by a nozzle position adjusting mechanism that adjusts the position of an end portion of the introduction nozzle in the flow passage of the flow cell.

19. The optical information analyzing method according to any one of claims 13 to 16,
wherein the step (c) adjusts the position of the end portion of the introduction nozzle in the flow passage so that the sample flow is positioned at a desired position relative to the measurement region, by an optimum offset jig selected among a plurality of offset jigs where the introduction nozzle is mounted and the position of the end portion of the mounted introduction nozzle varies and which adjusts the position of the end portion of the introduction nozzle in the flow passage of the flow cell by being fixed to the flow cell.

* * * * *